United States Patent [19]
Walker

[11] Patent Number: 5,891,921
[45] Date of Patent: *Apr. 6, 1999

[54] QUATERNARY AMMONIUM CARBOXYLATE AND BORATE COMPOSITIONS AND PREPARATION THEREOF

[75] Inventor: Leigh E. Walker, Macungie, Pa.

[73] Assignee: Lonza Inc., Anneandale, N.J.

[ * ] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,700,841.

[21] Appl. No.: 635,430

[22] Filed: Apr. 18, 1996

Related U.S. Application Data

[62] Division of Ser. No. 74,136, Jun. 9, 1993, Pat. No. 5,641,726.

[51] Int. Cl.$^6$ .................................................. A01N 33/12
[52] U.S. Cl. ......................... 514/642; 106/2; 106/15.05; 106/18.32; 252/194; 252/380; 252/403; 422/1; 424/405; 428/541; 504/158; 514/546; 514/547; 514/549; 514/552; 514/557; 514/558; 514/560; 514/574; 514/643; 554/1; 554/121; 554/122; 554/223; 554/224; 554/230; 560/129; 560/205; 560/225; 560/231; 560/261; 562/590; 562/597; 562/598; 562/601; 562/606; 562/607; 562/609
[58] Field of Search ..................................... 564/282, 288, 564/291, 296; 106/2, 15.05, 18.32; 252/194, 380, 403; 422/1; 424/405; 428/541; 504/158; 514/642, 643, 546, 547, 549, 552, 557, 558, 560, 574; 554/121, 122, 1, 223, 224, 230; 560/129, 205, 225, 231, 261; 562/590, 597, 598, 601, 606, 607, 609

[56] References Cited

U.S. PATENT DOCUMENTS

| | | | |
|---|---|---|---|
| 2,994,699 | 8/1961 | De Benneville | 260/294.7 |
| 3,169,983 | 2/1965 | Hunter | 260/462 |
| 3,233,645 | 2/1966 | Kalberg | 252/117 |
| 3,281,458 | 10/1966 | Jordan et al. | 260/501 |
| 3,301,815 | 1/1967 | Hunyar et al. | 260/45.9 |
| 3,646,147 | 2/1972 | Dadekian | 260/583 R |
| 4,585,795 | 4/1986 | Linderborg | 514/558 |
| 4,929,454 | 5/1990 | Findlay | 424/638 |
| 5,004,760 | 4/1991 | Patton et al. | 521/149 |

FOREIGN PATENT DOCUMENTS

| | | |
|---|---|---|
| 0293192 | 11/1988 | European Pat. Off. |
| 618433 | 2/1949 | United Kingdom |
| 650304 | 2/1951 | United Kingdom |
| 669506 | 4/1952 | United Kingdom |
| 719617 | 12/1954 | United Kingdom |
| 795814 | 5/1958 | United Kingdom |

OTHER PUBLICATIONS

Preston et al. (American Wood Preservers 'Assn) 83:331–348 (1987).
ASKO, Quaternary Ammonium Compounds—Fine and Functional Chemicals, 1991.
L. Jin & K. Archer, "Copper Based Wood Preservatives: Observation on Fixation, Distribution and Performance" preprints for *American Wood–Preservers' Association* Apr. 1991 meeting.
D.D. Nicholas et al., "Distribution and Permanency of DDAC in Southern Pine Sapwood Treated by the Full–Cell Process", *Forest Products Journal* 41 (1):41–45 (Jan. 1991).
L. Jin & A.F. Preston, "The Interaction of Wood Preservatives With Lignocellulosic Substrates" *Holzforschung* 45 (6):455–459.
*Proc. Amer. Wood–Preservers Assoc.* 80:191–209 (1984).
Y. Nakama, F. Harusawa & I. Murotani, "Cloud Point Phenomena In Mixtures of Anionic and Cationic Surfactants in Aqueous Solution" *JAOCS* 67 (11):717–721, (Nov. 1990).
A.F. Preston et al., "Recent Research On Alkylammonium Compounds In The U.S.", *American Wood–Preservers' Association*, 83:331–348 (1987).

(List continued on next page.)

*Primary Examiner*—Peter O'Sullivan
*Attorney, Agent, or Firm*—Darby & Darby

[57] ABSTRACT

Wood preservative systems comprising (a) a biocidal effective amount of (i) at least one di $C_8$–$C_{12}$ alkyl quaternary ammonium carboxylate having the formula

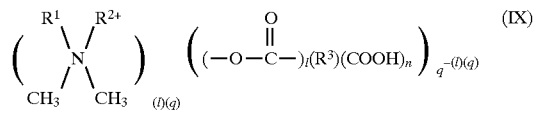

wherein $R^1$ and $R^2$ are a $C_8$–$C_{12}$ alkyl group; $R^3$ is a substituted or unsubstituted, interrupted or uninterrupted $C_1$–$C_{100}$ group; l and q independently are 1, 2 or 3 and (l)(q) is 1, 2, or 3; and n is 0 or an integer from 1 to 50; (ii) at least one di $C_8$–$C_{12}$ alkyl quaternary ammonium borate having the formula

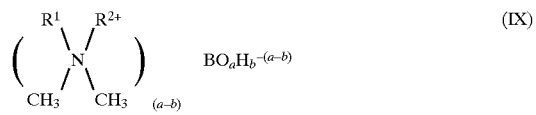

wherein $R^1$ and $R^2$ are defined as above, and a is 2 or 3, but when a is 2, b is 0 or 1, and when a is 3, b is 0, 1, or 2; or (iii) a combination of (i) and (ii); and (b) a solvent are provided. These carboxylate quats as well as carboxylate quats wherein $R^1$ is a $C_1$–$C_{20}$ alkyl or aryl-substituted alkyl group and $R^2$ is a $C_8$–$C_{20}$ alkyl group are preferably prepared by an indirect or a direct synthesis. The indirect synthesis includes reacting a corresponding quaternary ammonium carbonate with a carboxylic acid, while the direct synthesis method includes reacting a corresponding quaternary ammonium chloride with a metal carboxylate salt. The metal-free wood preservative systems can be applied to wood substrates.

3 Claims, 2 Drawing Sheets

OTHER PUBLICATIONS

"Quaternary Ammonium Compounds, Fine & Functional Chemicals" *AKZO*, pp. 1, 3–20 (1991).

D.D. Miller et al., "Control of Aggregate Structure With Mixed Counterions In An Ionic Double–Chained Surfactant", *Langmuir* 4(6):1363–1367 (1988).

Ewa Z. Radlinska et al., "Supra–Self Assembly: Vesicle–Micelle Equilibrium", *Colloids and Surfaces* 46:213–217 (1990).

J.E. Brady et al., "Counterion Specificity As The Determinant of Surfactant Aggregation" *J. Phys. Chem.* 90:1853–1859, (1986).

D.D. Miller et al., "Fluorescence Quenching In Double–Chained Surfactants. 1. Theory of Quenching In Micelles and Vesicles" *J. Phys. Chem.* 93:323–325 (1989).

J.E. Brady et al., "Spontaneous Vesicles", *J. American Chemical Society* 106:4279–4280 (1984).

A.F. Preston, "Dialkyldimethylammonium Halides As Wood Preservatives", *JAOCS* 60 (3):567–570 (Mar. 1983).

D.D. Nicholas & A.F. Preston, "Interaction of Preservatives With Wood" *Chemistyr of Solid Wood*, pp. 307–320 (1984).

E.W. Anacker and H.M. Ghose, "Counterions and Micelle Size I. Light Scattering by Solutions of Dodecyltrimethylammonium Salts", vol. 67 pp. 1713–1715, (Aug. 1963).

L. Sepulveda et al., "A New and Rapid Method for Preparing Long–Chain Alkyltrimethylammonium Salts With A Variety of Counterions", *Journal of Colloid and Interface Science* 117 (2):460–463 (Jun. 1987).

E. Jugerman et al., *Cationic Surfactants*, pp. 56–57, Marcel Dekker Inc. (1969).

"Quaternary Ammonium Compounds", *K.O.* 19:521–531 (1982).

"Quaternary Ammonium Compounds", *K.O.* 16:859–865 (1968).

Astle, "Industrial Organic Nitrogen Compounds", Reinhold Publ. pp. 64–67 (1961).

"Organic Reactions" 11, Chaptr. 5, Krieger Publ. Co., pp. 376–383 (1960).

Carl Kaiser et al., "Alkenes via Hofmann Elimination: Use of Ion–Exchange Resin For Preparation Of Quaternary Ammonium Hydroxides: Diphenylmethyl Vinyl Ether", *Organic Synthesis*, Collective vol. VI, pp. 552–554, John Wiley, Inc. (1988).

Y. Talmon et al., "Spontaneous Vesicle Formed From Hydroxide Surfactants: Evidence From Electron Microscopy" *Science* 221:1047–1048 (Sep. 9, 1983).

Awata et al., "Cathodic Esterification of Carboxylic Acids", *Chemistry Letters*, pp. 371–374 (1985).

A.W. Ralston et al., "The Solubilities of Long–Chain Dialkyldimethyl–Ammonium Chlorides In Organic Solvents", Contribution from the Research Laboratory of Armour and Company 13:186–190 (1948).

A.W. Ralston et al., "Conductivities of Quaternary Ammonium Chlorides Containing Two Long–Chain Alkyl Groups", Contribution from the Research Laboratory of Armour and Company 70:977–979 (Mar. 1948).

*Organic Chemistry* 35:3597–3598 (1941).

T.P Schultz et al., "Role of Stilbenes in the Natural Durability of Wood: Fungicidal Structure—Activity Relationships", *PhytoChemistry* 29:1501–1507 (1990).

85: 123253x "A Simple Preparation of Anhydrous Tetraalkylammonium Salts" (Abstract) (1976).

115: 87485b "Wood Preservatives Containing Quaternary Ammonium Salts With Polymers" (Abstract) (1991).

112: 212470j "Agrochemical Fungicides Containing Quaternary Ammonium Salts" (Abstract) (1990).

113: 153776j "Microbicidal Thermoplastic Resin Compositions" (Abstract) (1990).

112: 79768u "Noncorrosive Quaternary Ammonium Compounds As Wood Preservatives" (Abstract) (1990).

113: 163999y "Capacitor Driving Electrolytes and Their Preparation" (Abstract) (1990).

112: 54969x "Preparation of Quaternary Ammonium Hydroxides Free of Halogens" (Abstract) (1990).

110: 212114e Process For Producing Quaternary Salts (Abstract) (1989).

114: 246824j "Preparation of Carbonic Half–Esters of Betaine Structure" (Abstract) (1991).

98: 200032x "Didecyldimethylammonium Chloride—A Quaternary Ammonium Wood Preservative" (Abstract) (1983).

91: 152627b "Efficacy Acidic and Alkaline Solutions of Alkylammonium Compounds As Wood Preservatives" (Abstract) (1979).

113: 154360f Microbicidal Coating Compositions Containing Quaternary Ammonium Salts (Abstract) (1990).

109: 124403x "Quaternary Ammonium Salt–Containing Wood Preservatives" (Abstract) (1988).

103: 109954k "Clear Aqueous Disinfectant Solutions Containing Chlorhexidine Lactate Or Gluconate And Quaternary Ammonium Salts" (Abstract) (1989).

70: 111034d "Quaternary Ammonium Bases Compatible With Scintillation–Counting Liquids" (Abstract) (1969).

60: 16447d "Nematocidal Quaternary Ammonium Salts" (Abstract) (1964).

91: 109311g "Composition For Removing Water From Surfaces Of Articles" (Abstract) (1979).

75: 119170u "Corrosion–Resistant Lubricants and Antistatic Agents" (Abstract) (1971).

66: 66227y "Stabilization of Vinyl Resins With Organic Quaternary Ammonium Nitrates" (Abstract) (1967).

66: 1953n "N–Alkyl Ammonium Humates" (Abstract) (1967).

70: 111034d "Quaternary Ammonium Bases Compatible With Scintillation–Counting Liquids" (Abstract) (1969).

97: 91725 "Perfluoroallkyl Alkanols" (Chem. Abst.) (1982).

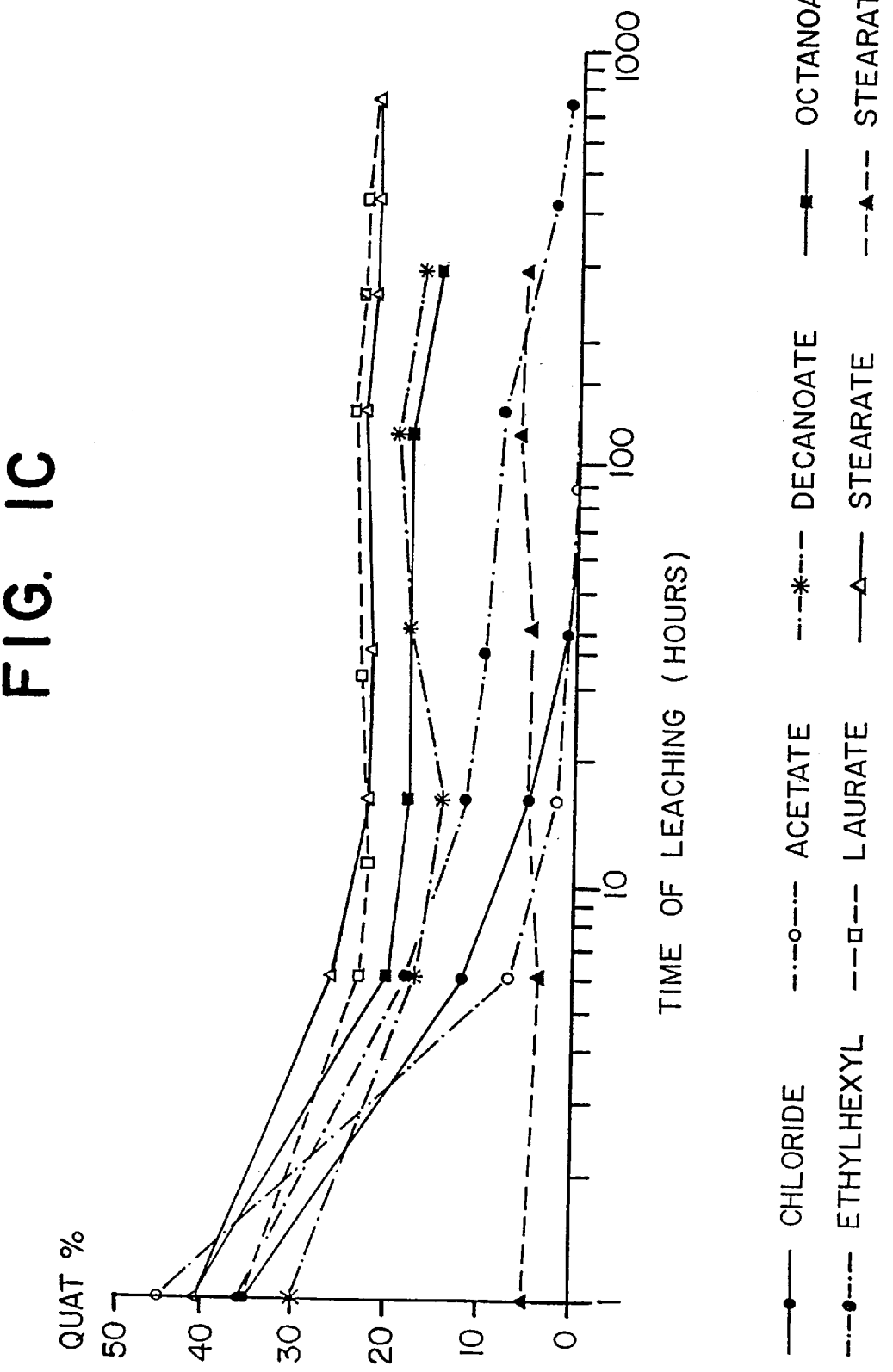

QUATERNARY AMMONIUM CARBOXYLATE AND BORATE COMPOSITIONS AND PREPARATION THEREOF

This is a division of application Ser. No. 08/074,136, filed Jun. 9, 1993 now U.S. Pat. No. 5,641,726.

Table of Related Applications

| Attorney's Docket No. | Appln. No. | Dated Filed | Title | Inventors |
|---|---|---|---|---|
| 5408/07421 | | Concurrently herewith | Quaternary Ammonium Hydroxide Compositions and Preparation Thereof | Leigh E. Walker |
| 5408/07423 | | Concurrently herewith | Quaternary Ammonium Carbonate Compositions and Preparation Thereof | Leigh E. Walker |
| 5408/07426 | | Concurrently herewith | WaterProofing and Preservative Compositions and Preparation Thereof | Leigh E. Walker |

FIELD OF THE INVENTION

This invention relates to di $C_8$–$C_{12}$ alkyl quaternary ammonium carboxylate(s) (carboxylate quat(s)) and di $C_8$–$C_{12}$ alkyl quaternary ammonium borate(s) (borate quat (s)) which are useful in metal-free wood preservative systems, as surfactants, and as biocides. These wood preservative systems are leaching resistant. Additionally, this invention relates to the synthesis of $C_1$–$C_{20}$ alkyl or aryl-substituted alkyl, $C_8$–$C_{20}$ alkyl carboxylate or borate quats from corresponding quaternary ammonium chlorides.

BACKGROUND OF THE INVENTION

Quaternary ammonium compounds (quats), and particularly didecyldimethylammonium chloride (DDAC)

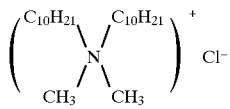

(I)

are commonly used as wood preservatives because they possess resistance properties to fungi and termites, to loss of strength, and to electrical sensitivity similar to those of commonly used acidic copper/chromium/arsenic solution (CCA) or ammoniacal copper and arsenic salt solution preservatives. See *Proc of the Am. Wood Pres. Assoc.*, 80:191–210 (1984). Although chloride quats do not include potentially dangerous heavy metals, didecyldimethylammonium chloride leaches rapidly in soil (Nicholas et al., *Forest Prod. J.*, 41:41 (1991), and therefore, does require coupling with copper salt.

Findlay et al., U.S. Pat. No. 4,929,454, disclose a method of preserving wood by impregnation with a quaternary ammonium compound and at least one of zinc and copper, wherein the quat anion is chosen from the group consisting of hydroxide, chloride, bromide, nitrate, bisulfate, acetate, bicarbonate, and carbonate, formate, borate and fatty acids. These quats have distinct environmental and safety advantages over commonly used acidic copper/chromium/arsenic solution (CCA) or ammoniacal copper and arsenic salt solution preservatives in that potentially dangerous heavy metals are not included. The Findlay et al. quats require copper or zinc in order to render them relatively insoluble and to prevent them from leaching out of a treated substrate. The use of copper or zinc in the above formulations may yet raise environmental and corrosion concerns.

Additionally, didecyldimethylammonium chloride tends to absorb preferentially to the surface of the wood and does not uniformly treat the whole substrate. Finally, DDAC treated wood shows a surface erosion or ages upon exposure to light. See Preston et al., *Proc. Am. Wood Pres. Assoc.*, 83:331 (1987).

The biocidal activities of various chloride quats against bacteria, fungi, and algae are tabulated in *Cationic Surfactants*, E. Jungerman Ed., pp. 56–57, Marcel Dekker, Inc., 1969. Nicholas, "Interaction of Preservatives with Wood," *Chemistry of Solid Wood*, Advances in Chemistry Series #207, Powell ed., (A.C.S. 1984), notes that didecyldimethylammonium compounds and particularly DDAC are potential biocides. Preston, J.A.O.C.S. 60:567 (1983), concurs and suggests that maximum fungitoxicity is exhibited with dialkyldimethyl compounds having $C_{10}$–$C_{12}$ alkyl groups. Butcher et al., Chem Abstracts No. 91:152627b, suggest that the presence of an acid or a base can affect the activity of didecyldimethylammonium quats.

Didecyldimethylammonium acetate was used as a phase transfer catalyst for an oxidation in Chem Abstracts No. 97:9175. A wood preservative was prepared by autoclaving didecylmethylamine with gluconic acid and ethylene oxide in isopropanol to yield $(C_{10}H_{21})_2 CH_3N (CH_2)_2O)^+$ gluconate in Chem Abstracts No. 109:124403x, while disinfectant solutions were prepared by exchanging a benzylammonium chloride with a chlorhexidene gluconate in Chem Abstracts No. 103:109954f.

Microbiocidal compositions which include quaternary ammonium compounds of the formula $R^1N^+R^2R^3R^4$ $X^-$, wherein at least one of $R^1$, $R^2$, or $R^3$ is a $C_8$–$C_{30}$ alkyl or alkenyl group and the remainder of $R^1$, $R^2$ or $R^3$ is methyl, ethyl, $CH_2Ph$ or 4-pyridylmethyl; $R^4$ is methyl or ethyl; and X is an anion of an acid having a $C_7$ or greater hydrophobic group, were disclosed in Chem Abstracts Nos. 113:154360f and 113:153776j. Chem Abstracts No. 112:79768u discloses compounds of the formula $R^1R^2R^3R^4N^+X^-$, wherein $R^1$, $R^2$, and $R^3$ are methyl, ethyl, benzoyl, 4-pyridinomethyl and at least one is $C_8$–$C_{30}$ alkyl or alkenyl; $R^4$ is methyl or ethyl; and X is a counter anion of acids having $C_7$ or greater hydrophobic groups. Dimethyldidecylammonium dodecylbenzenesulfonate was demonstrated to impart long term rot resistance to wood without causing rust, while the chloride salts of similar compounds were demonstrated to cause rust.

Patton et al., U.S. Pat. No. 5,004,760, disclose polymeric foams incorporating various dialkyldimethylammonium carboxylates such as didecyldimethylammonium poly (ethylene/acetate) and the like.

Quaternary ammonium compounds (quats) are typically prepared by the reaction:

$$R^1R^2R^3N + R^4X \rightarrow R^1R^2R^3R^4NX \quad (II)$$

wherein X is a halogen, a sulfate, a sulfo compound, or the like. When at least one of $R^1$, $R^2$, $R^3$, or $R^4$ is $C_{12}$ or longer, the product is an inert soap. Many of the inert soaps have biocidal activity against bacteria, fungi, algae, and related organisms.

Reaction (II) above is limited by the reactant $R^4X$ because $R^4$ must react with tertiary amines. For example, methyl chloride ($R^4X = CH_3Cl$) will react with a tertiary amine at less than 100° C. to yield a quaternary compound $R_3N^+CH_3$ $Cl^-$, while methanol or methyl acetate ($R^4X = CH_3OH$ or $CH_3COOCH_3$) will not, under similar reaction conditions.

General quaternary ammonium compounds with a sulfo group are easily prepared either by the reaction of a sulfate compound with a tertiary amine (III) or by a double exchange (IV).

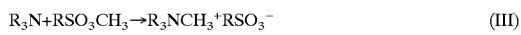
(III)

(IV)

If trimethylamine is heated with carbon dioxide and methanol above 200° C. and at 85 to 95 atmospheres, the carbonate quat, bis-tetramethylammonium carbonate, is prepared. *Industrial Organic Nitrogen Compounds*, Astle Ed. p 66, Reinhold Inc, 1961. However, this reaction is limited to the methyl compound because higher homologs decompose to olefins by the Hofman elimination reaction. See, *Organic Reactions*, 11, Chptr. 5, 377, Krieger Publishing Co., 1975.

Chem Abstracts 110:212114 (1989) suggests that dimethyl carbonate will react with triethylamine in methanol in twelve hours at 115° C. and under pressure to yield a methyl carbonate ester quat.

Chem Abstracts 114:24824 (1991) discloses that 6-hydroxylhexyldimethylamine reacts with dimethyl carbonate to yield a carbonate ester quat.

Quaternary ammonium hydroxides (hydroxy quats), an intermediate in the reaction scheme of the present invention, are currently prepared by the reaction of quaternary ammonium iodide with silver oxide (V).

$RN^+(CH_3)_3\ I^-+AgO \rightarrow RN^+(CH_3)_3OH^-+AgI$ (V)

However, this reaction is costly, and it is difficult to recover the silver reagent. See, *Organic Reactions*, 11:Chptr 5, pp. 376–377, Krieger Publishing Co., 1975.

In an olefin synthesis, it has been suggested to treat a quaternary salt with aqueous sodium or potassium followed by pyrolysis in order to form the hydroxy quat and then to decompose the hydroxy quat directly. However, in this method the hydroxy quat is not isolated and the conditions for its preparation are undesirable. See, *Organic Reactions*, 11:Chptr 5, pp. 376–377, Krieger Publishing Co., 1975.

Talmon et al., *Science*, 221, 1047 (1983), have used an ion exchange resin to convert didecyldimethylammonium bromide to didecyldimethylammonium hydroxide (VI).

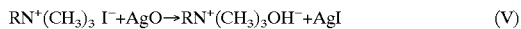
(VI)

However, 50 ml of ion exchange resin and two treatment steps were required to convert 3 grams of quaternary ammonium chloride to the corresponding hydroxide. Talmon et al. state that the hydroxy quat can be reacted with acids to make quats with different anions, and they have prepared didodecyldimethylammonium (DDDA) acetate, DDDA-formate, DDDA-propionate, DDDA-butyrate, DDDA-oxalate, DDDA-acrylate, DDDA-tartrate, DDDA-benzoate, and DDDA-octanoate. See also, *Organic Synthesis*, Collective Volume VI, 552, John Wiley Inc., 1988; Brady et al., J. Am. Chem. Soc., 106:4280–4282, 1984; Brady et al., *J. Phys. Chem.*, 90:9, 1853–1859, 1986; Miller et al., *J. Phys. Chem*, 91:1, 323–325, 1989; Radlinske et al., *Colloids and Surfaces*, 46:213–230, 1990.

Distearyldimethylammonium gluconate was prepared via ion exchange and subsequent reaction with an organic acid in Chem Abstracts No. 75:119170U. Miller et al, *Langmuir*, 4:1363 (1988) prepared ditetradecyldimethylammonium acetate by ion exchange from a bromide.

Alternatively, quaternary ammonium hydroxide compositions have been prepared by treating a haloquat in an electrochemical cell with special cation exchange diaphragms between the cells. The hydroxy quat collects at one electrode, and the halide collects at the other. Hydroxy quats, $R^1R^2R^3R^4N^+OH^-$, wherein the R groups were $C_1$–$C_4$, were treated with carboxylic acids to make asymmetric quats that were used as capacitor driving electrolytes. See, Japanese Patent Publication No. 02-106,915 and Awata et al., *Chemistry. Letters*, 371 (1985). Awata et al. placed carboxylic acids in the cathode cell to react with tetraethylammonium hydroxide as it was formed.

Japanese Patent Publication No. 01-172,363 discloses the preparation of relatively low yields of tetraethylammonium hydroxide by reacting triethylamine with diethyl sulfate, heating the resultant quat with sulfuric acid to yield the sulfate quat, and reacting the sulfate quat with barium hydroxide to yield the short chain quat, tetraethylammonium hydroxide, and barium sulfate.

Di $C_8$–$C_{,12}$ alkyl quaternary ammonium hydroxides prepared by ion exchange were used as strong bases to digest animal tissue by Bush et al., French Patent Publication No. 1,518,427.

Akzo discloses that the addition of a metallic hydroxide to a quaternary ammonium chloride such as didecyldimethylammonium chloride, in an aqueous medium, results in an equilibrium mixture of quaternary ammonium chloride and quaternary ammonium hydroxide (VII). This reaction can be driven to the right by the use of isopropanol as a solvent.

(VII)

Akzo further discloses that the addition of a soap to a quaternary ammonium chloride yields a quaternary ammonium carboxylate (VIII).

(VIII)

Jordan et al., U.S. Pat. No. 3,281,458, disclose the preparation of dioctadecyldimethylammonium humate, ditallowdimethylanmonium humate, dipentadecyldimethylammonium humate, and didodecyldimethylammonium humate by reacting humic acid, lignite, aqueous sodium hydroxide and a chloride quat.

Finally, Nakama et al., J.A.C.O.S., 67:717 (1990) report the interaction between anionic and cationic surfactant and particularly sodium laureate and stearyltrimethylammonium chloride, while Linderborg, U.S. Pat. No. 4,585,795, disclose the use of synergistic mixtures of the alkali metal salt of certain biocidal organic acids, quaternary ammonium chlorides, and alkyl-pyridinium chlorides as control agents for short-term protection of timber against sapstain fungi and mildew.

It has now been discovered that di $C_8$–$C_{12}$ alkyl quaternary ammonium carboxylates and/or borates can be incorporated into metal-free wood preservative systems. $C_1$–$C_{20}$ alkyl or aryl-substituted alkyl, $C_8$–$C_{20}$ alkyl carboxylate quats, and particularly the di $C_8$–$C_{12}$ alkyl carboxylate quats above, can be prepared by various methods from $C_1$–$C_{20}$ alkyl or aryl-substituted alkyl, $C_8$–$C_{20}$ alkyl quaternary ammonium chloride (chloride quat(s)) starting materials, including by indirect synthesis through $C_1$–$C_{20}$ alkyl or aryl-substituted alkyl, $C_8$–$C_{20}$ alkyl quaternary ammonium hydroxide and $C_1$–$C_{20}$ alkyl or aryl-substituted alkyl, $C_8$–$C_{20}$ alkyl quaternary ammonium carbonate intermediates or by direct synthesis. $C_1$–$C_{20}$ alkyl or aryl-substituted alkyl, $C_8$–$C_{20}$ alkyl borate quats, and particularly the di $C_8$–$C_{12}$ alkyl borate quats above can be prepared by various methods from $C_1$–$C_{20}$ alkyl or aryl-substituted alkyl, $C_8$–$C_{20}$ alkyl quaternary ammonium hydroxide starting materials, which may be prepared as above from the corresponding chloride quats. The di $C_8$–$C_{12}$ alkyl carbonate and/or borate quats, including those prepared by the methods above, are useful as wood preservatives, as they have improved leaching resistance, particularly without the use of the commonly used metal stabilizers or couplers, arsenic, chromium, copper, and zinc or combinations thereof.

BRIEF DESCRIPTION OF THE DRAWINGS

FIG. 1C is a graphic comparison of leaching of preservative systems according to the present invention and alternative wood preservative systems.

SUMMARY OF THE INVENTION

Figure 1A:
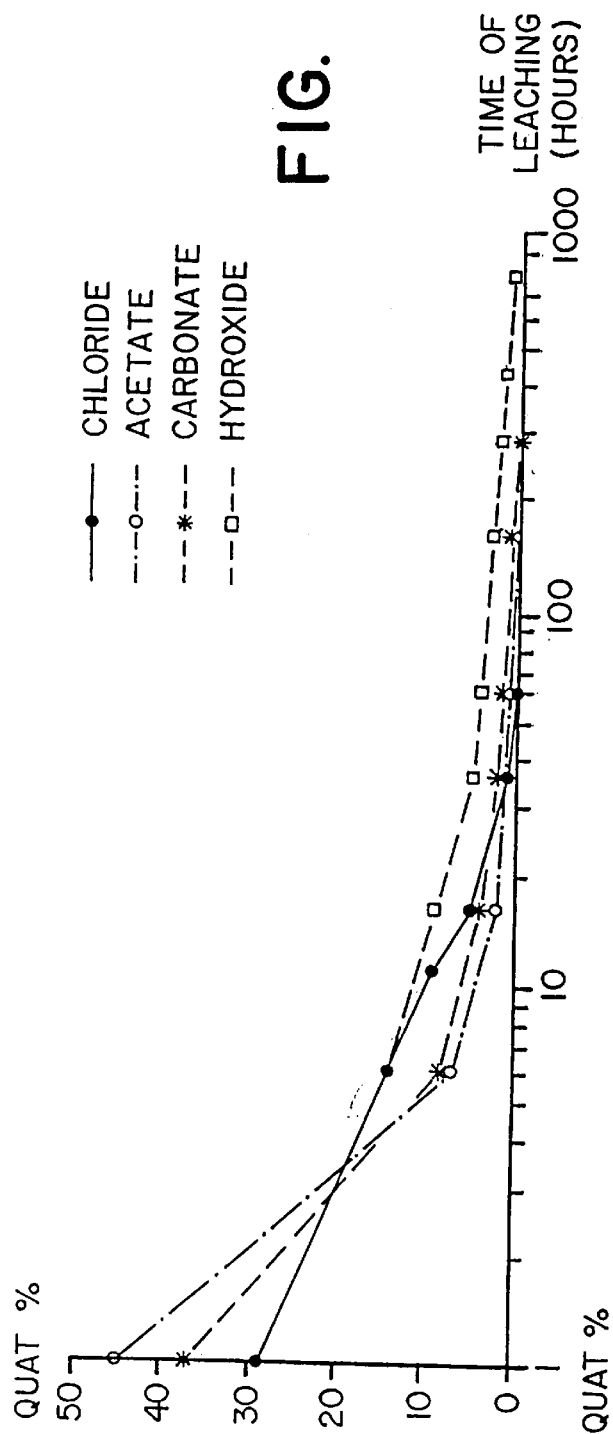
FIG. 1A is a graphic comparison of leaching of preservative systems according to the present invention and wood preservative systems of the prior art.

Wood preservative systems comprising (a) a biocidal effective amount of (i) at least one di $C_8$–$C_{12}$ alkyl quaternary ammonium carboxylate having the formula

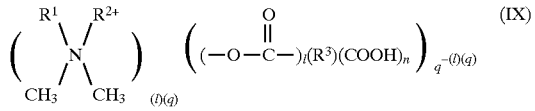

wherein $R^1$ is a $C_1$–$C_{20}$ alkyl or aryl-substituted alkyl group; $R^2$ is a $C_8$–$C_{20}$ alkyl group, but preferably $R^1$ and $R^2$ are the same $C_8$–$C_{12}$ alkyl group; $R^3$ is a substituted or unsubstituted, interrupted or uninterrupted $C_1$–$C_{100}$ group; l and q independently are 1, 2 or 3 and (l) (q) is 1, 2, or 3; and n is 0 or an integer from 1 to 50, and (b) a solvent; (ii) at least one di $C_8$–$C_{12}$ alkyl quaternary ammonium borate having the formula

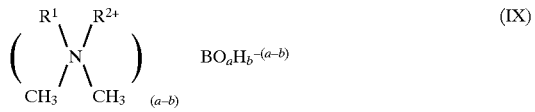

wherein $R^1$ and $R^2$ are defined as above, a is 2 or 3, but when a is 2, b is 0 or 1 and when a is 3, b is 0, 1, or 2; or (iii) a combination of (i) and (ii) are provided.

These carboxylate quats are preferably prepared by indirect or direct synthesis. The indirect synthesis comprises reacting two reactants, a $C_1$–$C_{20}$ alkyl or aryl-substituted alkyl, $C_8$–$C_{20}$ alkyl, and preferably a di $C_8$–$C_{12}$ alkyl, quaternary ammonium chloride and a metal hydroxide, in a solvent comprising a $C_1$–$C_4$ normal alcohol. The amount of metal hydroxide reactant is that amount sufficient to yield a $C_1$–$C_{20}$ alkyl or aryl-substituted alkyl, $C_8$–$C_{20}$ alkyl quaternary ammonium hydroxide (hydroxide quat(s)); and preferably a di $C_8$–$C_{12}$ alkyl quaternary ammonium hydroxide; a metal chloride; and optionally unreacted metal hydroxide. The resultant quaternary ammonium hydroxide and any unreacted metal hydroxide are then reacted with carbon dioxide to yield a $C_1$–$C_{20}$ alkyl or aryl-substituted alkyl, $C_8$–$C_{20}$ alkyl quaternary ammonium carbonate, and preferably a di $C_8$–$C_{12}$ alkyl quaternary ammonium carbonate; and optionally a metal carbonate. The resultant quaternary ammonium carbonate is reacted with carboxylic acid(s) having the formula $$((R^3)(COOH)_{(l+n)})_q \qquad (X)$$

wherein $R^3$, l, n, and q are defined as above, to yield the carboxylate quat.

Alternatively, the direct synthesis method comprises reacting a $C_1$–$C_{20}$ alkyl or aryl-substituted alkyl, $C_8$–$C_{20}$ alkyl quaternary ammonium chloride, and preferably a di $C_8$–$C_{12}$ alkyl quaternary ammonium chloride, with at least one metal carboxylate having the formula

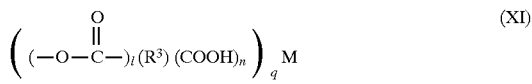

wherein $R^3$ and n are as defined above; M is a mono- di-, or tri-valent metal; l and q independently are 1, 2, or 3; and (l) (q) is 1 if M is mono-valent, 2 if M is di-valent, and 3 if M is tri-valent.

These borate quats are preferably prepared by a hydroxy/borate synthesis wherein a hydroxide quat as described above is reacted with boric acid.

Also contemplated by the invention is a method for preserving a wood substrate. Accordingly, the substrate is treated with a wood preservative system which comprises the above di $C_8$–$C_{12}$ alkyl quaternary ammonium carbonate and/or borate wood preservative system, and preferably those that include a carboxylate quat and/or borate quat prepared by the methods above.

DETAILED DESCRIPTION OF THE INVENTION

I. Wood Preservative Systems and Treatment of Substrates

Quaternary ammonium carboxylates (carboxylate quats) having the formula

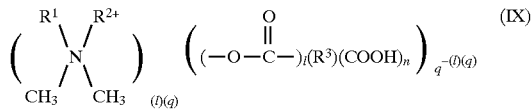

wherein $R^1$ is a $C_1$–$C_{20}$ alkyl or aryl-substituted alkyl group; $R^2$ is a $C_8$–$C_{20}$ alkyl group, but preferably $R^1$ and $R^2$ are the same $C_8$–$C_{12}$ alkyl group; $R^3$ is a substituted or unsubstituted, interrupted or uninterrupted $C_1$–$C_{100}$ group; l and q independently are 1, 2 or 3 and (l) (q) is 1, 2, or 3; and n is 0 or an integer from 1 to 50, and quaternary ammonium borates (borate quats) having the formula

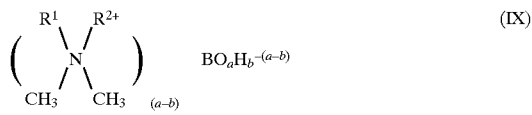

wherein $R^1$ and $R^2$ are defined as above, a is 2 or 3, but when a is 2, b is 0 or 1 and when a is 3, b is 0, 1, or 2, have been identified for use in wood preservative systems. These carboxylate and/or borate quats do not require metal couplers to render them leach resistant.

A preferred carboxylate quat is didecyldimethylammonium carboxylate wherein $R^1$ and $R^2$ are a $C_{10}$ alkyl group and most preferably an n-$C_{10}$ alkyl group, and a preferred borate quat is didecyldimethylammonium borate wherein $R^1$ and $R^2$ are a $C_{10}$ alkyl group and most preferably an n-$C_{10}$ alkyl group.

Preferred carboxyl anions are derived from saturated or unsaturated mono- or poly-, including, but not limited to, di- or tri-, carboxylic acids, and particularly $C_1$–$C_{20}$ carboxylic acids, or anhydrides thereof. $R^3$ independently can be substituted, particularly by one or more oxygen or boron atoms or sulfate groups, or interrupted, particularly by one or more oxygen or boron atoms or sulfate groups. Special mention is made of acetic acid, gluconic acid, lauric acid, formic acid, propionic acid, butyric acid, oxalic acid, acrylic acid, tartaric acid, benzoic acid, octanoic acid, and the like.

Additionally, the carboxyl group can be derived from polymeric acids or copolymers in which one or more of the monomers is an acid. An example of a polyacid is polyacrylic acid. Examples of copolymer acids include, but are not limited to, olefin/carboxylic acid polymers such as poly(ethylene/acrylic acid).

Such acids, including the polymeric or copolymeric acids mentioned above, are of the formula $$((R^3)(COOH)_{(l+n)})_q \quad (X)$$

where $R^3$, l, n, and q are defined as above. In polymeric or copolymeric carboxylic acids, $R^3$ can be represented as $((R^4)_x(R^5)_y)$ giving $$((R^4)_x(R^5)_y(COOH)_{(l+n)})_q \quad (XII)$$

where $R^4$ and $R^5$ independently are substituted or unsubstituted, interrupted or uninterrupted as above $C_1$–$C_{100}$ groups and x and y independently are 0 or integers from 1 to 100, but both x and y are not 0. Preferably, $R^3$, $R^4$, and $R^5$ independently are alkyl or alkenyl groups.

These carboxylate and/or borate quats can be formulated as metal-free wood preservative systems. These systems include a biocidal effective amount of at least one carboxylate and/or borate quat and a suitable solvent including aqueous and non-aqueous solvents. Preferably, the solvent is an aqueous solvent including, but not limited to, water, aqueous alcohol, such as ethyl alcohol, ammonia water, aqueous acetic acid, and the like, or a combination of any of the foregoing.

Although other conventional additives may be added to these systems as required for application to different substrates and for different uses as known to those of ordinary skill in the art, metal stabilizers are not required and, in fact, are not recommended to inhibit leaching of the quat from the substrate. Accordingly, wood substrates, such as lumber, timber, and the like, can be treated with metal-free preservative systems which comprise the above carboxylate and/or borate quat(s) diluted in a suitable solvent as above.

The amount of quaternary ammonium carboxylate(s) and/or borate(s) used to treat the substrate is a biocidal effective amount, i.e. that amount effective to inhibit the growth of or to kill one or more organism that causes wood rot, to inhibit sap stain, or a combination thereof. Such organisms include, but are not limited to, *Trametes viride* or *Trametes versicolor*, which cause a white rot; *Goeophyllium trabeum*, which causes a brown rot; and *Aspergillus niger*, which causes sap stain/mold.

Typically, a wood preservative system will comprise from about 0.1 to about 5 parts by weight of the carboxylate and/or borate quat(s) and from about 95 to about 99.9 parts by weight of solvent based upon 100 parts by weight of quat(s) and solvent combined. Most preferably, the wood preservative system of the present invention will comprise from about 1 to about 2 parts by weight of carboxylate and/or borate quat(s) and from about 98 to about 99 parts by weight of solvent on the same basis.

Treatment of the substrate is accomplished by any means known to those of ordinary skill in the art including, but not limited to, dipping, soaking, brushing, pressure treating, or the like. The length of treatment required will vary according to treatment conditions, the selection of which are known to those skilled in the art.

The metal-free wood preservative systems of the present invention display greater resistance to leaching than wood preservatives currently used in the industry. Resistance to leaching is defined as retention of a biocidal effective amount, and preferably at least about 2% by weight of carboxylate and/or borate quat(s) in the substrate over a prolonged period of at least about 100 hours and preferably about 350 hours. Applicants hypothesize, without being bound by any theory, that the carboxylate and/or borate quat(s) may not absorb as quickly to the outside of wood as do conventional wood preservatives, permitting a more complete and uniform treatment of the wood. They may also bond to the wood directly or through hydrogen bonding to help anchor the quat. Unsaturation in the anion will allow for oxidation and/or polymerization reactions to occur and to fix the quat. It is also believed that the long chain carboxylate quat(s) and the wood preservative systems that include such quats enhance waterproofing properties of treated substrates.

II. Synthesis

A. Indirect Synthesis

Although carboxylate quats can be prepared by a variety of methods, applicants have discovered an indirect synthesis method that can be used to prepare a variety of $C_1$–$C_{20}$ alkyl or aryl-substituted alkyl, $C_8$–$C_{20}$ alkyl, preferably di $C_8$–$C_{12}$ alkyl, quaternary ammonium carboxylates, and most preferably didecyldimethylammonium carboxylate.

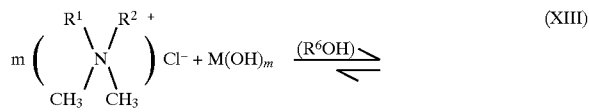

(XIII)

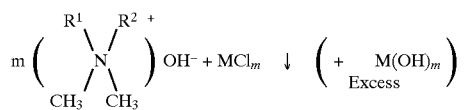

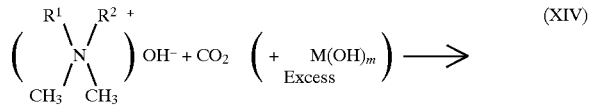

(XIV)

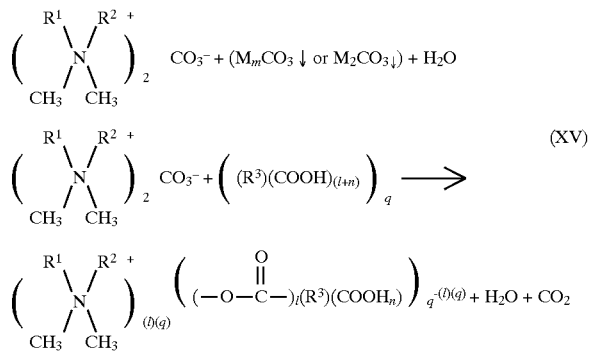

(XV)

wherein $R^1$ is a $C_1$–$C_{20}$ alkyl or aryl-substituted alkyl group; $R^2$ is a $C_8$–$C_{20}$ alkyl group, and preferably $R^1$ and $R^2$ are the same $C_8$–$C_{12}$ alkyl group; $R^6$ is a straight chain $C_1$–$C_4$ alkyl group; $R^3$ is a substituted or unsubstituted, as explained above, interrupted or uninterrupted, as explained above, $C_1$–$C_{100}$ group; l and q independently are 1, 2, or 3 and (l)(q) is 1, 2, or 3; M is a mono-, bi-, tri-valent metal, preferably a monovalent metal, and most preferably an alkali metal; n is 0 or an integer from 1 to 50; and m is 1 if M is mono-valent, 2 if M is di-valent, and 3 if M is tri-valent.

The carboxylate quat is prepared via a carbonate quat intermediate. The carbonate quat intermediate is more stable, and particularly more thermal stable, than the hydroxy quat intermediate and can be stored for longer periods of time than the hydroxy quat intermediate. Consequently, a "universal" intermediate can be stored for particular carboxylate quat preparation when the indirect synthesis method is used.

A $C_1$–$C_{20}$ alkyl or aryl-substituted alkyl, $C_8$–$C_{20}$ alkyl, and preferably a di $C_8$–$C_{12}$ alkyl, quaternary ammonium chloride is used as a starting material and is reacted with a metal hydroxide to yield a $C_1$–$C_{20}$ alkyl or aryl-substituted alkyl, $C_8$–$C_{20}$ alkyl, and preferably a di $C_8$–$C_{12}$ alkyl, quaternary ammonium hydroxide intermediate. The hydroxy quat first intermediate(s) and any excess metal hydroxide are then reacted with carbon dioxide to yield carbonate quat second intermediate(s) and metal carbonate(s). The carbonate quat second intermediate(s) is then reacted with at least one carboxylic acid to yield the carboxylate quat(s).

Many $C_1$–$C_{20}$ alkyl or aryl-substituted alkyl, $C_8$–$C_{20}$ alkyl quaternary ammonium chlorides are suitable reactants to prepare the first intermediate hydroxy quat, but di $C_8$–$C_{12}$ alkyl quaternary ammonium chlorides are preferred and didecyldimethylammonium chloride is most preferred. Special mention is made of di-n-decyldimethylammonium chloride. The selection of the $C_8$–$C_{12}$ alkyl substituent of the chloride quat reactant is determinative of the hydroxy quat first intermediate, therefore, of the carbonate quat second intermediate, and ultimately, of the cation component of the carboxylate quat product.

Special mention is also made of processes wherein $R^1$ is a methyl, $C_8$ alkyl, $C_9$ isoalkyl, $C_{10}$ alkyl, $C_{12}$ alkyl, $C_{14}$ alkyl, $C_{16}$ alkyl or a benzyl group; and $R^2$ is a $C_{10}$ alkyl, $C_{12}$ alkyl, $C_{14}$ alkyl or $C_{16}$ alkyl group.

The metal hydroxide reactant is a mono-, bi-, or tri-valent metal hydroxide, preferably a mono-valent metal hydroxide, and most preferably an alkali metal hydroxide such as sodium hydroxide or potassium hydroxide. Special mention is made of potassium hydroxide. The metal chloride first step reaction product will precipitate and is easily removed, i.e. by filtration or the like, yielding a hydroxy quat/solvent reaction product. The hydroxy quat can be separated therefrom by drying or the like, if desired.

The preparation of the hydroxy quat is preferably conducted in a solvent which comprises a $C_1$–$C_4$ normal alcohol. Preferably the solvent is ethanol, and most preferably, anhydrous ethanol. The reaction to form the hydroxy quat is typically an equilibrium reaction, but the use of a $C_1$–$C_4$ normal alcohol solvent drives the reaction sharply to the hydroxy quat.

The amount of metal hydroxide reactant typically is a stoichiometric amount with respect to the di $C_8$–$C_{12}$ alkyl quaternary ammonium chloride reactant. Therefore, on a theoretical basis and if the reaction were complete and unequilibrated, there would be no excess of metal hydroxide reactant upon completion of the first intermediate reaction. In practice, yield of hydroxy quat when using a stoichiometric amount of metal hydroxide reactant will range from about 65% to about 95%.

Yield of the hydroxy quat can be further improved over conventional methods by utilization of a stoichiometric excess of metal hydroxide ranging from about 2% to about 20% excess. If an excess of metal hydroxide is used yield will be increased to from about 95% to about 99%.

The unreacted metal hydroxide is soluble in the hydroxy quat/solvent intermediate.

Hydroxy quat and any unreacted metal hydroxide are then reacted with at least a stoichiometric equivalent of carbon dioxide to yield the quaternary ammonium carbonate(s), and if any unreacted metal hydroxide were present, the metal carbonate(s). The conversion of the metal hydroxide to the metal carbonate is the preferred reaction of the two carbonations and will proceed more rapidly. The metal carbonate will precipitate and can be separated easily, i.e. by filtration or the like, leaving the stable carbonate quat(s) or carbonate quat(s)/solvent reaction product. The carbonation step can also produce the bicarbonate quat(s) or the metal carbonate quat(s) as by-products.

The carbonate quat second intermediate(s) is then reacted with at least a stoichiometric amount of carboxylic acid(s) to yield the carboxylate quat(s). Carboxylic acid reactants are of formulas (X) or (XII) as described and explained above. The selection of the carboxylic acid(s) will be determinative of the quat anion.

Typically in the indirect synthesis, the reactants and solvent of the chloride quat to hydroxy quat reaction (the first reaction) (XIII) will be stirred and heated to from about 20° C. to about 70° C. and held at that temperature for a period of from about 1 hour to about 5 hours. The reaction mixture is then cooled, first to room temperature and then to about 0° C. where it is held for about 1 hour to about 2 hours. Any precipitated metal chloride is collected as is known in the art, i.e. such as by filtration.

Alternatively, the first reaction reactants and solvent can be stirred at a slightly elevated temperature, i.e. from about 20° C. to about 40° C., to yield the hydroxy quat(s)/solvent mixture. Hydroxy quat can be separated as above.

The carbon dioxide in reaction (XIV) is generally bubbled through the hydroxy quat(s)/solvent supernatant for a suitable period known to those of ordinary skill in the art, typically varying from about 0.5 hour to about 1 hour, at ambient temperature. Alternately, the carbon dioxide can be added as solid dry ice directly to the hydroxy quat. Any precipitated metal carbonate is collected as is known in the art, i.e. such as by filtration.

The carboxylic acid(s) in reaction (Xv) is typically added over a short period of several minutes, and the reaction typically is rapid. The carboxylate quat(s) can be separated or concentrated by filtration or evaporation after a carbon dioxide evolution in this step is completed.

In the indirect synthesis, any acid having a pKa less than that of carbonic acid, i.e., less than 6.4, such as carboxylic, phosphoric, sulfonic acids, and the like, can be reacted with a carbonate quat and displace carbon dioxide.

The addition of ammonia will retard the carbonate quat and acid reaction (XV). For example, if ammonia is added to a mixture of a polyacid and a carbonate quat, the acid-carbonate quat reaction is retarded. However, when ammonia is slowly evaporated, the reaction liberating carbon dioxide may proceed, yielding a compound that is fixed (insoluble) in wood. Similarly, a system of polyacid and acetic acid should yield an insoluble polyacid quat when the acetic acid evaporates.

B. Direct Synthesis

Alternatively, a direct synthesis method for the production of the carboxylate quat(s) has been discovered. A metal salt of a carboxylic acid is reacted with a $C_1$–$C_{20}$ alkyl or aryl-substituted alkyl, $C_8$–$C_{20}$ alkyl, and preferably a di-$C_8$–$C_{12}$ alkyl, quaternary ammonium chloride, in a double replacement reaction, to yield the carboxylate quat and the metal chloride salt

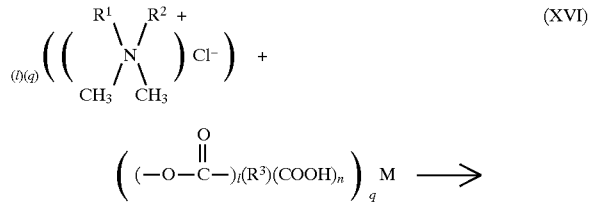

$$\left(\begin{array}{c}R^1\phantom{XX}R^2\phantom{X}+\\ \phantom{X}\diagdown\phantom{X}\diagup\phantom{X}\\ \phantom{XX}N\\ \phantom{X}\diagup\phantom{X}\diagdown\phantom{X}\\ CH_3\phantom{XX}CH_3\end{array}\right)_{(l)(q)}\left(\begin{array}{c}O\\ \|\\ (-O-C-)_l(R^3)(COOH)_n\end{array}\right)_q^{-(l)(q)}+MCl_{(l)(q)}\downarrow$$

wherein $R^1$, $R^2$, $R^3$, M, l, q, and n are as defined above.

The metal carboxylates are derived from carboxylic acids. The carboxylic acids are as described and detailed above. The metals are mono-, di-, or the tri-valent metals, preferably mono-valent metals and most preferably alkali metals. Special mention is made of potassium and sodium.

Reaction (XVI) can be conducted neat or in a number of solvents including, but not limited to ethanol, acetic acid, or propionic acid. Preferably, the solvent comprises a $C_1$–$C_4$ normal alcohol as described above. Yield will depend on the solvent and the reaction conditions selected, which can be determined by one of ordinary skill in the art through routine experimentation in accordance with this detailed explanation.

The chloride quat starting material is selected as above, and again, its selection is determinative of the cation of the carboxylate quat to be formed.

C. Hydroxy Quat/Acid Synthesis of Carboxylates

Finally, a third method for the production of the carboxylate quat(s) which includes reacting hydroxy quat(s) with carboxylic acid(s) has been discovered.

$$\begin{array}{c}R^1\phantom{XX}R^2+\\ \phantom{X}\diagdown\phantom{X}\diagup\phantom{X}\\ \phantom{XX}N\\ \phantom{X}\diagup\phantom{X}\diagdown\phantom{X}\\ CH_3\phantom{XX}CH_3\end{array}OH^-+\left(\begin{array}{c}(R^3)(COOH)_{(l+n)}\end{array}\right)_q\longrightarrow \quad (XVII)$$

$$\left(\begin{array}{c}R^1\phantom{XX}R^2\phantom{X}+\\ \phantom{X}\diagdown\phantom{X}\diagup\phantom{X}\\ \phantom{XX}N\\ \phantom{X}\diagup\phantom{X}\diagdown\phantom{X}\\ CH_3\phantom{XX}CH_3\end{array}\right)_{(l)(q)}\left(\begin{array}{c}O\\ \|\\ (-O-C-)_l(R^3)(COOH)_n\end{array}\right)_q^{-(l)(q)}+H_2O$$

wherein $R^1$, $R^2$, $R^3$, l, q, and n are as defined above.

The hydroxy quat(s), carboxylic acid(s), and carboxylate quat(s) are as described above.

D. Hydroxy Quat/Acid Synthesis of Borate Quats

Borate quats are preferably prepared by reacting hydroxy quat(s) with boric acid.

$$\begin{array}{c}R^1\phantom{XX}R^2+\\ \phantom{X}\diagdown\phantom{X}\diagup\phantom{X}\\ \phantom{XX}N\\ \phantom{X}\diagup\phantom{X}\diagdown\phantom{X}\\ CH_3\phantom{XX}CH_3\end{array}OH^-+BO_3H_3\longrightarrow \quad (XVII)$$

$$\left(\begin{array}{c}R^1\phantom{XX}R^2\phantom{X}+\\ \phantom{X}\diagdown\phantom{X}\diagup\phantom{X}\\ \phantom{XX}N\\ \phantom{X}\diagup\phantom{X}\diagdown\phantom{X}\\ CH_3\phantom{XX}CH_3\end{array}\right)_{(a-b)}BO_aH_b{}^{-(a-b)}+H_2O$$

where $R^1$, $R^2$, a and b are defined as above.

The hydroxy quat(s) and borate quat(s) are as described above.

Mixing, adding, and reacting of the components in any of the methods of the present invention can be accomplished by conventional means known to those of ordinary skill in the art. The order of addition of reactants or solvent in any individual step does not affect the process. Reactants and/or solvent can be added sequentially or simultaneously in any suitable reaction vessel. For example, the metal hydroxide in the indirect synthesis may be dissolved in alcohol and the resultant mixture added to the chloride quat or the chloride quat may be dissolved in alcohol and the metal hydroxide added to the resultant mixture. Importantly, the methods of the present invention are suitable for commercial scale production techniques and equipment, yet convenient for small scale work.

DESCRIPTION OF THE PREFERRED EMBODIMENTS

The following examples illustrate the invention without limitation. All parts and percentages are given by weight unless otherwise indicated.

Quaternary compounds are quantified by two phase titration with sodium laurylsulfate and an indicator. The mixture is buffered to a pH of 10.

Indirect Synthesis of Carboxylate Quat

EXAMPLE 1

Didecyldimethylarmonium propionate 180 grams (0.4 mole) of 80% didecyldimethylammonium chloride in 20% ethanol water (144 grams of DDAC), 180 ml of absolute denatured ethanol (denatured with methanol/isopropanol), and 32 grams (0.49 mole) of 85% potassium hydroxide pellets (27 grams of KOH) were mixed in a flask that was purged with nitrogen and equipped with a heating mantle and a magnetic stirrer. The mixture was stirred and heated at 60°–70° C. for three hours. The mixture was then allowed to cool to room temperature and finally cooled to 5° C.

Potassium chloride precipitated, and the precipitate was collected on a vacuum filter. The solid was washed with cold ethanol and subsequently was dried, yielding 31 grams (calculated yield 29.6 grams) of dry potassium chloride.

The ethanolic solution of the hydroxy quat containing about 0.09 mole of unreacted KOH, was stirred while 50 grams of carbon dioxide (from sublimed carbon dioxide) were bubbled over one half hour. The resultant mixture was then filtered to remove 7.2 grams of potassium carbonate (6.2 grams calculated), and the filtrate was concentrated to yield an orange/brown liquid with 80–85% carbonate quat (0.4 mole of carbonate quat) and less than 0.1% chloride for a product with 98 to 99% exchanged quat purity.

The cold product, after filtration, was placed in a closed flask equipped with a condenser, addition funnel, and a tube connected to a water displacement type gas measuring device. An equivalent (0.4 mole, 29.6 grams), of propionic acid was added to the carbonate quat over five minutes. Immediate gas evolution was noted, and 5.75 liters of gas were collected over 15 minutes. The solvent was removed on a rotary evaporator after the carbon dioxide evolution ceased, and yielded a yellow/orange liquid.

Quat analysis revealed that the product contained 85% active quat with 0.09% free chloride and 99% exchange.

EXAMPLE 2

Didecyldimethylammonium acetate

The procedure of Example 1 is followed, substituting 0.4 mole of acetic acid for the propionic acid.

EXAMPLE 3

Didecyldimethylammonium 2-ethylhexanoate

The procedure of Example 1 is followed, substituting 0.4 mole of 2-ethylhexanoic acid for the propionic acid.

The product is cloudy.

EXAMPLE 4

Didecyldimethylammonium gluconate

The procedure of Example 1 is followed, substituting 0.4 mole of gluconic acid for the propionic acid.

The product is water soluble.

EXAMPLE 5
Didecyldimethylammonium octanoate

The procedure of Example 1 is followed, substituting 0.4 mole of octanoic acid for the propionic acid.

EXAMPLE 6

Didecyldimethylammonium mixed coconut fatty acid carboxylate

The procedure of Example 1 is followed, substituting 0.4 mole of mixed coconut fatty acid for the propionic acid.

EXAMPLE 7
Didecyldimethylammonium laurate

The procedure of Example 1 is followed, substituting 0.4 mole of lauric acid for the propionic acid.

The product is a waxy solid.

EXAMPLE 8
Didecyldimethylammonium stearate

The procedure of Example 1 is followed, substituting 0.4 mole of stearic acid for the propionic acid.

The product is a waxy solid.

EXAMPLE 9
Didecyldimethylammonium linolenate

The procedure of Example 1 is followed, substituting 0.4 mole of linolenic acid for the propionic acid.

The product is an orange brown liquid.

EXAMPLE 10
Didecyldimethylammonium linoleate

The procedure of Example 1 is followed, substituting 0.4 mole of linoleic acid for the propionic acid.

The product is an orange brown liquid.

EXAMPLE 11
Didecyldimethylammonium adipate

The procedure of Example 1 is followed, substituting 0.4 mole of adipic acid for the propionic acid.

The product is a solid.

EXAMPLE 12
Didecyldimethylammonium adipate

The procedure of Example 1 is followed, substituting 0.8 mole of adipic acid for the 0.4 mole of propionic acid.

The product is a solid.

EXAMPLE 13
Didecyldimethylammonium citrate

The procedure of Example 1 is followed, substituting 0.4 mole of citric acid for the propionic acid.

EXAMPLE 14
Didecyldimethylammonium citrate

The procedure of Example 1 is followed, substituting 0.8 mole of citric acid for the propionic acid.

EXAMPLE 15
Didecyldimethylammonium citrate

The procedure of Example 1 is followed, substituting 1.2 moles of citric acid for the propionic acid.

EXAMPLE 16
Didecyldimethylammonium polyacrylate

The procedure of Example 1 is followed, substituting a low molecular weight polyacylic acid for the propionic acid.

The product is solid and is insoluble in water.

EXAMPLE 17
Octyldecyldimethylammonium propionate

The procedure of Example 1 was followed, substituting 0.4 mole of 80% octyldecyldimethylammonium chloride for the didecyldimethylammonium chloride to yield octyldecyldimethylammonium propionate.

EXAMPLE 18
Octyldecyldimethylammonium acetate

The procedure of Example 2 was followed, substituting 0.4 mole of 80% octyldecyldimethylammonium chloride for the didecyldimethylammonium chloride to yield octyldecyldimethylammonium acetate.

EXAMPLE 19
Octyldecyldimethylammonium 2-ethylhexanoate

The procedure of Example 3 was followed, substituting 0.4 mole of 80% octyldecyldimethylammonium chloride for the didecyldimethylammonium chloride to yield octyldecyldimethylammonium 2-ethylhexanoate.

EXAMPLE 20
Octyldecyldimethylammonium gluconate

The procedure of Example 4 was followed, substituting 0.4 mole of 80% octyldecyldimethylammonium chloride for the didecyldimethylammonium chloride to yield octyldecyldimethylammonium gluconate.

EXAMPLE 21
Octyldecyldimethylammonium octanoate

The procedure of Example 5 was followed, substituting 0.4 mole of 80% octyldecyldimethylammonium chloride for the didecyldimethylammonium chloride to yield octyldecyldimethylammonium octanoate.

EXAMPLE 22
Octyldecyldimethylammonium mixed coconut fatty acid carboxylate

The procedure of Example 6 was followed, substituting 0.4 mole of 80% octyldecyldimethylammonium chloride for the didecyldimethylammonium chloride to yield octyldecyldimethylammonium mixed coconut fatty acid carboxylate.

EXAMPLE 23
Octyldecyldimethylammonium laurate

The procedure of Example 7 was followed, substituting 0.4 mole of 80% octyldecyldimethylammonium chloride for the didecyldimethylammonium chloride to yield octyldecyldimethylammonium laurate.

EXAMPLE 24
Octyldecyldimethylammonium stearate

The procedure of Example 8 was followed, substituting 0.4 mole of 80% octyldecyldimethylammonium chloride for the didecyldimethylammonium chloride to yield octyldecyldimethylammonium stearate.

EXAMPLE 25
Octyldecyldimethylammonium linolenate

The procedure of Example 9 was followed, substituting 0.4 mole of 80% octyldecyldimethylammonium chloride for the didecyldimethylammonium chloride to yield octyldecyldimethylammonium linolenate.

EXAMPLE 26
Octyldecyldimethylammonium linoleate

The procedure of Example 10 was followed, substituting 0.4 mole of 80% octyldecyldimethylammonium chloride for the didecyldimethylammonium chloride to yield octyldecyldimethylammonium linoleate.

EXAMPLE 27
Octyldecyldimethylammonium adipate

The procedure of Example 11 was followed, substituting 0.4 mole of 80% octyldecyldimethylammonium chloride for the didecyldimethylammonium chloride to yield octyldecyldimethylammonium adipate.

EXAMPLE 28
Octyldecyldimethylammonium citrate

The procedure of Example 13 was followed, substituting 0.4 mole of 80% octyldecyldimethylammonium chloride for the didecyldimethylammonium chloride to yield octyldecyldimethylammonium citrate.

EXAMPLE 29
Octyldecyldimethylammonium polyacrylate

The procedure of Example 16 was followed, substituting 0.4 mole of 80% octyldecyldimethylammonium chloride for the didecyldimethylammonium chloride to yield octyldecyldimethylammonium polyacrylate.

EXAMPLE 30
Isononyldecyldimethylanmonium propionate

The procedure of Example 1 was followed, substituting 0.4 mole of 80% octadecyldimethylammonium chloride for the didecyldimethylammonium chloride to yield isononyldecyldimethylammonium propionate.

EXAMPLE 31
Isononyldecyldimethylammonium acetate

The procedure of Example 2 was followed, substituting 0.4 mole of 80% isononyldecyldimethylammonium chloride for the didecyldimethylammonium chloride to yield isononyldecyldimethylarmonium acetate.

EXAMPLE 32
Isononyldecyldimethylammonium 2-ethylhexanoate

The procedure of Example 3 was followed, substituting 0.4 mole of 80% isononyldecyldimethylammonium chloride for the didecyldimethylammonium chloride to yield isononyldecyldimethylammonium 2-ethyl-hexanoate.

EXAMPLE 33
Isononyldecyldimethylammonium gluconate

The procedure of Example 4 was followed, substituting 0.4 mole of 80% isononyldecyldimethylammonium chloride for the didecyldimethylammonium chloride to yield isononyldecyldimethylammonium gluconate.

EXAMPLE 34
Isononyldecyldimethylammonium octanoate

The procedure of Example 5 was followed, substituting 0.4 mole of 80% isononyldecyldimethylammonium chloride for the didecyldimethylammonium chloride to yield isononyldecyldimethylammonium octanoate.

EXAMPLE 35
Isononyldecyldimethylammonium mixed coconut fatty acid carboxylate The procedure of Example 6 was followed, substituting 0.4 mole of 80% isononyldecyldimethylanmonium chloride for the didecyldimethylammonium chloride to yield isononyldecyldimethylammonium mixed coconut fatty acid carboxylate.

EXAMPLE 36
Isononyldecyldimethylammonium laurate

The procedure of Example 7 was followed, substituting 0.4 mole of 80% isononyldecyldimethylammonium chloride for the didecyldimethylammonium chloride to yield isononyldecyldimethylammonium laurate.

EXAMPLE 37
Isononyldecyldimethylamnonium stearate

The procedure of Example 8 was followed, substituting 0.4 mole of 80% isononyldecyldimethylammonium chloride for the didecyldimethylammonium chloride to yield isononyldecyldimethylammonium stearate.

EXAMPLE 38
Isononyldecyldimethylammonium linolenate

The procedure of Example 9 was followed, substituting 0.4 mole of 80% isononyldecyldimethylammonium chloride for the didecyldimethylammonium chloride to yield isononyldecyldimethylammonium linolenate.

EXAMPLE 39
Isononyldecyldimethylammonium linoleate

The procedure of Example 10 was followed, substituting 0.4 mole of 80% isononyldecyldimethylammonium chloride for the didecyldimethylammonium chloride to yield isononyldecyldimethylammonium linoleate.

EXAMPLE 40
Isononyldecyldimethylammonium adipate

The procedure of Example 11 was followed, substituting 0.4 mole of 80% isononyldecyldimethylammonium chloride for the didecyldimethylammonium chloride to yield isononyldecyldimethylammonium adipate.

EXAMPLE 41
Isononyldecyldimethylammonium citrate

The procedure of Example 13 was followed, substituting 0.4 mole of 80% isononyldecyldimethylammonium chloride for the didecyldimethylammonium chloride to yield isononyldecyldimethylammonium citrate.

EXAMPLE 42
Isononyldecyldimethylammonium polyacrylate

The procedure of Example 16 was followed, substituting 0.4 mole of 80% isononyldecyldimethylammonium chloride for the didecyldimethylammonium chloride to yield isononyldecyldimethylammonium polyacrylate.

EXAMPLE 43
Benzyldodecyldimethylammonium propionate

The procedure of Example 1 was followed, substituting 0.4 mole of 80% benzyldodecyldimethylammonium chloride for the didecyldimethylammonium chloride to yield benzyldodecyldimethylammonium propionate.

EXAMPLE 44
Benzyldodecyldimethylammonium acetate

The procedure of Example 2 was followed, substituting 0.4 mole of 80% benzyldodecyldimethylammonium chloride for the didecyldimethylammonium chloride to yield benzyldodecyldimethylammonium acetate.

EXAMPLE 45
Benzyldodecyldimethylammonium 2-ethylhexanoate

The procedure of Example 1 was followed, substituting 0.4 mole of 80% benzyldodecyldimethylammonium chloride for the didecyldimethylammonium chloride to yield benzyldodecyldimethylammonium 2-ethylhexanoate.

EXAMPLE 46
Benzyldodecyldimethylammonium gluconate

The procedure of Example 4 was followed, substituting 0.4 mole of 80% benzyldodecyldimethylammonium chloride for the didecyldimethylammonium chloride to yield benzyldodecyldimethylammonium gluconate.

EXAMPLE 47
Benzyldodecyldimethylammonium octanoate

The procedure of Example 5 was followed, substituting 0.4 mole of 80% benzyldodecyldimethylammonium chloride for the didecyldimethylammonium chloride to yield benzyldodecyldimethylammonium octanoate.

EXAMPLE 48
Benzyldodecyldimethylammonium mixed coconut fatty acid carboxylate The procedure of Example 7 was followed, substituting 0.4 mole of 80% benzyldodecyldimethylammonium chloride for the didecyldimethylammonium chloride to yield benzyldodecyldimethylammonium mixed coconut fatty acid carboxylate.

EXAMPLE 49
Benzyldodecyldimethylammonium stearate

The procedure of Example 8 was followed, substituting 0.4 mole of 80% benzyldodecyldimethylammonium chloride for the didecyldimethylammonium chloride to yield benzyldodecyldimethylammonium stearate.

EXAMPLE 50
Benzyldodecyldimethylammonium linolenate

The procedure of Example 9 was followed, substituting 0.4 mole of 80% benzyldodecyldimethylammonium chloride for the didecyldimethylammonium chloride to yield benzyldodecyldimethylammonium linolenate.

EXAMPLE 51
Benzyldodecyldimethylammonium linoleate

The procedure of Example 10 was followed, substituting 0.4 mole of 80% benzyldodecyldimethylammonium chloride for the didecyldimethylammonium chloride to yield benzyldodecyldimethylammonium linoleate.

EXAMPLE 52
Benzyldodecyldimethylammonium adipate

The procedure of Example 11 was followed, substituting 0.4 mole of 80% benzyldodecyldimethylammonium chloride for the didecyldimethylammonium chloride to yield benzyldodecyldimethylammonium adipate.

EXAMPLE 53
Benzyldodecyldimethylammonium citrate

The procedure of Example 13 was followed, substituting 0.4 mole of 80% benzyldodecyldimethylammonium chloride for the didecyldimethylammonium chloride to yield benzyldodecyldimethylammonium citrate.

EXAMPLE 54
Benzyldodecyldimethylammonium polyacylate

The procedure of Example 16 was followed, substituting 0.4 mole of 80% benzyldodecyldimethylammonium chloride for the didecyldimethylammonium chloride to yield benzyldodecyldimethylammonium polyacylate.

EXAMPLE 55
A mixture of benzyldodecyl-, benzyltetradecyl-, and benzylhexadecyldimethylammonium propionate The procedure of Example 1 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium propionate.

EXAMPLE 56
A mixture of benzyldodecyl-, benzyltetradecyl-, and benzylhexadecyldimethylammonium acetate The procedure of Example 2 was followed, substituting 0.4 mole of 80% of a mixture of benzyldodecyl-, benzyltetradecyl-, and benzylhexadecyldimethylammonium acetate chloride for the didecyldimethylammonium chloride to yield a mixture of benzyldodecyl-, benzyltetradecyl-, and benzylhexadecyldimethylammonium acetate.

EXAMPLE 57
A mixture of benzyldodecyl-, benzyltetradecyl-, and benzylhexadecyldimethylammonium 2-ethylhexanoate The procedure of Example 3 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium 2-ethylhexanoate.

EXAMPLE 58
A mixture of benzyldodecyl-, benzyltetradecyl-, and benzylhexadecyldimethylammonium gluconate The procedure of Example 4 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium gluconate.

EXAMPLE 59
A mixture of benzyldodecyl-, benzyltetradecyl-, and benzylhexadecyldimethylammonium octanoate The procedure of Example 5 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium octanoate.

EXAMPLE 60
A mixture of benzyldodecyl-, benzyltetradecyl-, and benzylhexadecyldimethylammonium mixed coconut fatty acid carboxylate The procedure of Example 6 was followed, substituting 0.4 mole of 80% of a mixture of benzyldodecyl-, benzyltetradecyl-, and benzylhexadecyldimethylammonium mixed fatty acid benzyldodecyldimethylammonium chloride for the didecyldimethylammonium chloride to yield a mixture of benzyldodecyl-, benzyltetradecyl-, and benzylhexadecyldimethylammonium mixed coconut fatty acid carboxylate.

EXAMPLE 61
A mixture of benzyldodecyl-, benzyltetradecyl-, and benzylhexadecyldimethylanmonium laurate The procedure of Example 7 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium laurate.

EXAMPLE 62
A mixture of benzyldodecyl-, benzyltetradecyl-, and benzylhexadecyldimethylammonium stearate The procedure of Example 8 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium stearate.

EXAMPLE 63
A mixture of benzyldodecyl-, benzyltetradecyl-, and benzylhexadecyldimethylammonium linolenate The procedure of Example 9 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium linolenate.

EXAMPLE 64
A mixture of benzyldodecyl-, benzyltetradecyl-, and benzylhexadecyldimethylammonium linoleate The procedure of Example 10 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium linoleate.

EXAMPLE 65
A mixture of benzyldodecyl-, benzyltetradecyl-, and benzylhexadecyldimethylammonium adipate The procedure of Example 11 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium adipate.

EXAMPLE 66
A mixture of benzyldodecyl-, benzyltetradecyl-, and benzylhexadecyldimethylammonium citrate The procedure of Example 13 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium citrate.

EXAMPLE 67
A mixture of benzyldodecyl-, benzyltetradecyl-, and benzylhexadecyldimethylammonium polyacrylate The procedure of Example 17 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium polyacrylate.

EXAMPLE 68
Dihexadecyldimethylammonium propionate

The procedure of Example 1 was followed, substituting 0.4 mole of 80% dihexadecyldimethylammonium chloride for the didecyldimethylammonium chloride to yield dihexadecyldimethylammonium propionate.

EXAMPLE 69
Dihexadecyldimethylammonium acetate

The procedure of Example 2 was followed, substituting 0.4 mole of 80% dihexadecyldimethylammonium chloride for the didecyldimethylammonium chloride to yield dihexadecyldimethylammonium acetate.

EXAMPLE 70
Dihexadecyldimethylammonium 2-ethylhexanoate

The procedure of Example 3 was followed, substituting 0.4 mole of 80% dihexadecyldimethylammonium chloride for the didecyldimethylammonium chloride to yield dihexadecyldimethylammonium 2-ethylhexanoate.

EXAMPLE 71
Dihexadecyldimethylammonium gluconate

The procedure of Example 4 was followed, substituting 0.4 mole of 80% dihexadecyldimethylammonium chloride for the didecyldimethylammonium chloride to yield dihexadecyldimethylammonium gluconate.

EXAMPLE 72
Dihexadecyldimethylammonium octanoate

The procedure of Example 5 was followed, substituting 0.4 mole of 80% dihexadecyldimethylammonium chloride for the didecyldimethylammonium chloride to yield dihexadecyldimethylammonium octanoate.

EXAMPLE 73
Dihexadecyldimethylammonium mixed coconut fatty acid carboxylate

The procedure of Example 6 was followed, substituting 0.4 mole of 80% dihexadecyldimethylammonium chloride for the didecyldimethylammonium chloride to yield dihexadecyldimethylammonium mixed coconut fatty acid carboxylate.

EXAMPLE 74
Dihexadecyldimethylammonium laurate

The procedure of Example 7 was followed, substituting 0.4 mole of 80% dihexadecyldimethylammonium chloride for the didecyldimethylammonium chloride to yield dihexadecyldimethylammonium laurate.

EXAMPLE 75
Dihexadecyldimethylammonium stearate

The procedure of Example 8 was followed, substituting 0.4 mole of 80% dihexadecyldimethylammonium chloride for the didecyldimethylammonium chloride to yield dihexadecyldimethylammonium stearate.

EXAMPLE 76
Dihexadecyldimethylammonium linolenate

The procedure of Example 9 was followed, substituting 0.4 mole of 80% dihexadecyldimethylammonium chloride for the didecyldimethylammonium chloride to yield dihexadecyldimethylammonium linolenate.

EXAMPLE 77
Dihexadecyldimethylammonium linoleate

The procedure of Example 10 was followed, substituting 0.4 mole of 80% dihexadecyldimethylammonium chloride for the didecyldimethylammonium chloride to yield dihexadecyldimethylammonium linoleate.

EXAMPLE 78
Dihexadecyldimethylammonium adipate

The procedure of Example 11 was followed, substituting 0.4 mole of 80% dihexadecyldimethylammonium chloride for the didecyldimethylammonium chloride to yield dihexadecyldimethylammonium adipate.

EXAMPLE 79
Dihexadecyldimethylammonium citrate

The procedure of Example 13 was followed, substituting 0.4 mole of 80% dihexadecyldimethylammonium chloride for the didecyldimethylammonium chloride to yield dihexadecyldimethylammonium citrate.

EXAMPLE 80
Dihexadecyldimethylammonium polyacrylate

The procedure of Example 16 was followed, substituting 0.4 mole of 80% dihexadecyldimethylammonium chloride for the didecyldimethylammonium chloride to yield dihexadecyldimethylammonium polyacrylate.

EXAMPLE 81
Dodecyltrimethylammonium propionate

The procedure of Example 1 was followed, substituting 0.4 mole of 80% dodecyltrimethylammonium chloride for the didecyldimethylanmonium chloride to yield dodecyltrimethylammonium propionate.

EXAMPLE 82
Dodecyltrimethylammonium acetate

The procedure of Example 2 was followed, substituting 0.4 mole of 80% dodecyltrimethylammonium chloride for the didecyldimethylammonium chloride to yield dodecyltrimethylammonium acetate.

EXAMPLE 83
Dodecyltrimethylammonium 2-ethylhexanoate

The procedure of Example 3 was followed, substituting 0.4 mole of 80% dodecyltrimethylammonium chloride for the didecyldimethylammonium chloride to yield dodecyltrimethylammonium 2-ethylhexanoate.

EXAMPLE 84
Dodecyltrimethylammonium gluconate

The procedure of Example 4 was followed, substituting 0.4 mole of 80% dodecyltrimethylammonium chloride for the didecyldimethylammonium chloride to yield dodecyltrimethylammonium gluconate.

EXAMPLE 85
Dodecyltrimethylammonium octanoate

The procedure of Example 5 was followed, substituting 0.4 mole of 80% dodecyltrimethylammonium chloride for the didecyldimethylammonium chloride to yield dodecyltrimethylammonium octanoate.

EXAMPLE 86
Dodecyltrimethylammonium mixed coconut fatty acid carboxylate

The procedure of Example 6 was followed, substituting 0.4 mole of 80% dodecyltrimethylammonium chloride for the didecyldimethylammonium chloride to yield dodecyltrimethylammonium mixed coconut fatty acid carboxylate.

EXAMPLE 87
Dodecyltrimethylammonium laurate

The procedure of Example 7 was followed, substituting 0.4 mole of 80% dodecyltrimethylammonium chloride for the didecyldimethylammonium chloride to yield dodecyltrimethylammonium laurate.

EXAMPLE 88
Dodecyltrimethylammonium stearate

The procedure of Example 8 was followed, substituting 0.4 mole of 80% dodecyltrimethylammonium chloride for the didecyldimethylammonium chloride to yield dodecyltrimethylammonium stearate.

EXAMPLE 89
Dodecyltrimethylammonium linolenate

The procedure of Example 9 was followed, substituting 0.4 mole of 80% dodecyltrimethylammonium chloride for the didecyldimethylammonium chloride to yield dodecyltrimethylammonium linolenate.

EXAMPLE 90
Dodecyltrimethylammonium linoleate

The procedure of Example 10 was followed, substituting 0.4 mole of 80% dodecyltrimethylarnmonium chloride for the didecyldimethylammonium chloride to yield dodecyltrimethylammonium linoleate.

EXAMPLE 91
Dodecyltrimethylammonium adipate

The procedure of Example 11 was followed, substituting 0.4 mole of 80% dodecyltrimethylammonium chloride for the didecyldimethylammonium chloride to yield dodecyltrimethylammonium adipate.

EXAMPLE 92
Dodecyltrimethylammonium citrate

The procedure of Example 13 was followed, substituting 0.4 mole of 80% dodecyltrimethylammonium chloride for the didecyldimethylammonium chloride to yield dodecyltrimethylammonium citrate.

EXAMPLE 93
Dodecyltrimethylammonium polyacrylate

The procedure of Example 16 was followed, substituting 0.4 mole of 80% dodecyltrimethylammonium chloride for the didecyldimethylammonium chloride to yield dodecyltrimethylammonium polyacrylate.

Direct Synthesis of Carboxylate Quat

EXAMPLE 94
Didecyldimethylammonium acetate 180 grams (0.4 mole) of 80% didecyldimethylammonium chloride in 20% ethanol water (144 grams of DDAC), 180 ml of anhydrous ethanol, and a stoichiometric excess, 47 grams (0.48 mole), of anhydrous potassium acetate was mixed in a flask that was purged with nitrogen and equipped with a heating mantle, a magnetic stirrer, and a condenser. The mixture was stirred and heated at 60°–70° C. for two hours. The insoluble potassium acetate crystals slowly dissolved and a finer solid (KCl) separated. The mixture was then cooled to 0° C. and vacuum filtered. The solid washed with cold ethanol to remove 30.7 grams of potassium chloride (theoretical 29.6 grams). The solution was concentrated, cooled, and filtered to remove 6.5 grams of potassium acetate (theoretical 29.6 grams).

Additional fine crystals of potassium acetate settled out on standing. By assay, the light yellow liquid product was determined to be 80% quat with 100% exchange.

EXAMPLE 95
Didecyldimethylammonium acetate 0.0221 mole of potassium acetate and 0.0221 mole of 80% didecyldimethylammonium chloride in ethanol were mixed in a flask. The mixture was heated to 60° C.–70° C. and held for 1.5 hours.

The resultant quat was analyzed, and conversion was determined to be 94%.

EXAMPLE 96
Didecyldimethylammonium acetate 0.0221 mole of potassium acetate and 0.0221 mole of 80% didecyldimethylammonium chloride in solid form were mixed in a flask. The mixture was heated to 60° C.–70° C. and held for 1.5 hours.

The resultant quat was analyzed, and conversion was determined to be 92%.

EXAMPLE 97
Didecyldimethylammonium acetate 0.0221 mole of sodium acetate and 0.0221 mole of 80% didecyldimethylammonium chloride in solid form were mixed in a flask. The mixture was heated to 60° C. and held for 2 hours.

The resultant quat was analyzed, and conversion was determined to be 50%.

EXAMPLE 98
Didecyldimethylammonium acetate 0.0221 mole of sodium acetate and 0.0221 mole of 80% didecyldimethylammonium chloride in 5 ml of acetic acid were mixed in a flask. The mixture was heated to 60° C. and held for 1 hour.

The resultant quat was analyzed, and conversion was determined to be 93%.

EXAMPLE 99
Didecyldimethylammonium gluconate 0.0221 mole of sodium gluconate and 0.0221 mole of 80% didecyldimethylammonium chloride in water were mixed in a flask. The mixture was heated and held until evolution of carbon dioxide gas ceased.

The resultant quat was analyzed, and conversion was determined to be less than 20%.

EXAMPLE 100
Didecyldimethylammonium 2-ethylhexanoate 0.0221 mole of sodium 2-ethylhexanoate and 0.0221 mole of 80% didecyldimethylammonium chloride in water were mixed in a flask. The mixture was heated and held until evolution of carbon dioxide gas ceased.

The resultant quat was analyzed, and conversion was determined to be 77%.

EXAMPLE 101
Didecyldimethylammonium laurate 0.4 mole of sodium laurate and 0.4 mole of 80% didecyldimethylammonium chloride in water were mixed in a flask. The mixture was heated to 60° C. and held for 1 hour.

The resultant quat was analyzed, and conversion was determined to be 90%

EXAMPLE 102
Didecyldimethylammonium propionate 0.0221 mole of sodium propionate and 0.0221 mole of 80% didecyldimethylammonium chloride in 8 grams of propionic acid were mixed in a flask. The mixture was heated to 60° C.–80° C. and held for 2 hours.

The resultant quat was analyzed, and conversion was determined to be 90%

EXAMPLE 103
Didecyldimethylammonium propionate 0.4 mole of potassium propionate and 0.4 mole of 80% didecyldimethylammonium chloride in solid form were mixed in a flask. The mixture was heated to 60° C.–80° C. and held for 2 hours.

The resultant quat was analyzed, and conversion was determined to be 91%.

EXAMPLE 104
Octyldecyldimethylammonium acetate

The procedure of Example 94 was followed, substituting 0.4 mole of 80% octyldecyldimethylammonium chloride for the didecyldimethylammonium chloride to yield octyldecyldimethylammonium acetate.

EXAMPLE 105
Octyldecyldimethylammonium gluconate

The procedure of Example 99 was followed, substituting 0.0221 mole of 80% octyldecyldimethylammonium chloride for the didecyldimethylammonium chloride to yield octyldecyldimethylammonium gluconate.

EXAMPLE 106
Octyldecyldimethylammonium 2-ethylhexanoate

The procedure of Example 100 was followed, substituting 0.0221 mole of 80% octyldecyldimethylammonium chloride for the didecyldimethylammonium chloride to yield octyldecyldimethylammonium 2-ethylhexanoate.

EXAMPLE 107
Octyldecyldimethylammonium laurate

The procedure of Example 101 was followed, substituting 0.4 mole of 80% octyldecyldimethylammonium chloride for the didecyldimethylanmonium chloride to yield octyldecyldimethylammonium laurate.

EXAMPLE 108
Octyldecyldimethylammonium propionate

The procedure of Example 102 was followed, substituting 0.0221 mole of 80% octyldecyldimethylammonium chloride for the didecyldimethylammonium chloride to yield octyldecyldimethylammonium propionate.

EXAMPLE 109
Isononyldecyldimethylammonium acetate

The procedure of Example 94 was followed, substituting 0.4 mole of 80% isononyldecyldimethylammonium chloride for the didecyldimethylammonium chloride to yield isononyldecyldimethylammonium acetate.

EXAMPLE 110
Isononyldecyldimethylammonium gluconate

The procedure of Example 99 was followed, substituting 0.0221 mole of 80% isononyldecyldimethylammonium chloride for the didecyldimethylammonium chloride to yield isononyldecyldimethylammonium gluconate.

EXAMPLE 111
Isononyldecyldimethylammonium 2-ethyl hexanoate

The procedure of Example 100 was followed, substituting 0.0221 mole of 80% isononyldecyldimethylammonium chloride for the didecyldimethylammonium chloride to yield isononyldecyldimethylammonium hexanoate.

EXAMPLE 112
Isononyldecyldimethylammonium laurate

The procedure of Example 101 was followed, substituting 0.4 mole of 80% isononyldecyldimethylammonium chloride for the didecyldimethylammonium chloride to yield isononyldecyldimethylammonium laurate.

EXAMPLE 113
Isononyldecyldimethylammonium propionate

The procedure of Example 102 was followed, substituting 0.0221 mole of 80% isononyldecyldimethylammonium chloride for the didecyldimethylammonium chloride to yield isononyldecyldimethylammonium propionate.

EXAMPLE 114
Benzyldodecyldimethylammonium acetate

The procedure of Example 94 was followed, substituting 0.4 mole of 80% benzyldodecyldimethylammonium chloride for the didecyldimethylammonium chloride to yield benzyldodecyldimethylammonium acetate.

EXAMPLE 115
Benzyldodecyldimethylammonium gluconate

The procedure of Example 99 was followed, substituting 0.0221 mole of 80% benzyldodecyldimethylammonium chloride 10 for the didecyldimethylammonium chloride to yield benzyldodecyldimethylammonium gluconate.

EXAMPLE 116
Benzyldodecyldimethylammonium 2-ethylhexanoate

The procedure of Example 100 was followed, substituting 0.0221 mole of 80% benzyldodecyldimethylammonium chloride for the didecyldimethylammonium chloride to yield benzyldodecyldimethylammonium 2-ethylhexanoate.

EXAMPLE 117
Benzyldodecyldimethylammonium laurate

The procedure of Example 101 was followed, substituting 0.4 mole of 80% benzyldodecyldimethylammonium chloride for the didecyldimethylammonium chloride to yield benzyldodecyldimethylammonium laurate.

EXAMPLE 118
Benzyldodecyldimethylammonium propionate

The procedure of Example 102 was followed, substituting 0.0221 mole of 80% benzyldodecyldimethylammonium chloride for the didecyldimethylammonium chloride to yield benzyldodecyldimethylammonium propionate.

EXAMPLE 119
A mixture of benzyldodecyl-, benzyltetradecyl-, and benzylhexadecyldimethylammonium acetate The procedure of Example 94 was followed, substituting 0.4 mole of 80% of a mixture of benzyldodecyl-, benzyltetradecyl-, and benzylhexadecyldimethylammonium acetate chloride for the didecyldimethylammonium chloride to yield a mixture of benzyldodecyl-, benzyltetradecyl-, and benzylhexadecyldimethylammonium acetate.

EXAMPLE 120
A mixture of benzyldodecyl-, benzyltetradecyl-, and benzylhexadecyldimethylammonium gluconate The procedure of Example 99 was followed, substituting 0.0221 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium gluconate.

EXAMPLE 121
A mixture of benzyldodecyl-, benzyltetradecyl-, and benzylhexadecyldimethylammonium 2-ethylhexanoate The procedure of Example 100 was followed, substituting 0.0221 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium 2-ethylhexanoate.

EXAMPLE 122
A mixture of benzyldodecyl-, benzyltetradecyl-, and benzylhexadecyldimethylammonium laurate The procedure of Example 101 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium laurate.

EXAMPLE 123
A mixture of benzyldodecyl-, benzyltetradecyl-, and benzylhexadecyldimethylammonium propionate The procedure of Example 102 was followed, substituting 0.0221 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium propionate.

EXAMPLE 124
Dihexadecyldimethylammonium acetate

The procedure of Example 94 was followed, substituting 0.4 mole of 80% dihexadecyldimethylammonium chloride for the didecyldimethylammonium chloride to yield dihexadecyldimethylammonium acetate.

EXAMPLE 125
Dihexadecyldimethylammonium gluconate

The procedure of Example 99 was followed, substituting 0.0221 mole of 80% dihexadecyldimethylammonium chloride for the didecyldimethylammonium chloride to yield dihexadecyldimethylammonium gluconate.

EXAMPLE 126
Dihexadecyldimethylammonium 2-ethylhexanoate

The procedure of Example 100 was followed, substituting 0.0221 mole of 80% dihexadecyldimethylammonium chloride for the didecyldimethylammonium chloride to yield dihexadecyldimethylammonium 2-ethylhexanoate.

EXAMPLE 127
Dihexadecyldimethylammonium laurate

The procedure of Example 101 was followed, substituting 0.4 mole of 80% dihexadecyldimethylammonium chloride for the didecyldimethylammonium chloride to yield dihexadecyldimethylammonium laurate.

EXAMPLE 128
Dihexadecyldimethylammonium propionate

The procedure of Example 102 was followed, substituting 0.0221 mole of 80% dihexadecyldimethylammonium chloride for the didecyldimethylammonium chloride to yield dihexadecyldimethylammonium propionate.

EXAMPLE 129
Dodecyltrimethylammonium acetate

The procedure of Example 94 was followed, substituting 0.4 mole of 80% dodecyltrimethylammonium chloride for the didecyldimethylammonium chloride to yield dodecyltrimethylammonium acetate.

EXAMPLE 130
Dodecyltrimethylammonium gluconate

The procedure of Example 99 was followed, substituting 0.0221 mole of 809 dodecyltrimethylammonium chloride for the didecyldimethylammonium chloride to yield dodecyltrimethylammonium gluconate.

EXAMPLE 131
Dodecyltrimethylammonium 2-ethylhexanoate

The procedure of Example 100 was followed, substituting 0.0221 mole of 80% dodecyltrimethylammonium chloride for the didecyldimethylammonium chloride to yield dodecyltrimethylammonium 2-ethylhexanoate.

EXAMPLE 132
Dodecyltrimethylammonium laurate

The procedure of Example 101 was followed, substituting 0.4 mole of 80% dodecyltrimethylammonium chloride for the didecyldimethylammonium chloride to yield dodecyltrimethylammonium laurate.

EXAMPLE 133
Dodecyltrimethylammonium propionate

The procedure of Example 102 was followed, substituting 0.0221 mole of 80% dodecyltrimethylammonium chloride for the didecyldimethylammonium chloride to yield dodecyltrimethylammonium propionate.

Hydroxy Quat/Acid Synthesis

EXAMPLE 134
Didecyldimethylammonium propionate 180 grams (0.4 mole) of 80% didecyldimethylammonium chloride in 20% ethanol water (144 grams of DDAC), 180 ml of absolute denatured ethanol (denatured with methanol/isopropanol), and 26 grams (0.4 mole) of 85% potassium hydroxide pellets (22 grams of KOH) were mixed in a flask that was purged with nitrogen and equipped with a heating mantle and a magnetic stirrer. The mixture was stirred and heated at 60°–70° C. for three hours. The mixture was then allowed to cool to room temperature and finally cooled to 0° C. for at least one hour.

Potassium chloride precipitated, and the precipitate was collected on a vacuum filter. The solid was washed with cold ethanol and subsequently was dried, yielding 30 grams of dry potassium chloride.

The hydroxy quat/ethanol solution was mixed with a stoichiometric amount of propionic acid to yield a yellow/orange liquid having a flash point of 106° F.

EXAMPLE 135
Didecyldimethylammonium borate

The procedure of Example 134 is followed substituting 0.4 mole of boric acid for the propionic acid.

The product is a liquid.

EXAMPLE 136
Octyldecyldimethylammonium borate

The procedure of Example 135 was followed, substituting 0.4 mole of 80% octyldecyldimethylammonium chloride for the didecyldimethylammonium chloride to yield octyldecyldimethylammonium borate.

EXAMPLE 137
Isononyldecyldimethylammonium borate

The procedure of Example 135 was followed, substituting 0.4 mole of 80% isononyldecyldimethylammonium chloride for the didecyldimethylammonium chloride to yield isononyldecyldimethylammonium borate.

EXAMPLE 138
Benzyldodecyldimethylammonium borate

The procedure of Example 135 was followed, substituting 0.4 mole of 80% benzyldodecyldimethylammonium chloride for the didecyldimethylammonium chloride to yield benzyldodecyldimethylammonium borate.

EXAMPLE 139
A mixture of benzyldodecyl-, benzyltetradecyl-, and benzylhexadecyldimethylammonium borate The procedure of Example 135 was followed, substituting 0.4 mole of 80% of a mixture of benzyldodecyl-, benzyltetradecyl-, and benzylhexadecyldimethylammonium chloride for the didecyldimethylammonium chloride to yield a mixture of benzyldodecyl-, benzyltetradecyl-, and benzylhexadecyldimethylammonium borate.

EXAMPLE 140
Dihexadecyldimethylammonium borate

The procedure of Example 135 was followed, substituting 0.4 mole of 80% dihexadecyldimethylammonium chloride for the didecyldimethylammonium chloride to yield dihexadecyldimethylammonium borate.

EXAMPLE 141
Dodecyltrimethylammonium borate

The procedure of Example 135 was followed, substituting 0.4 mole of 80% dodecyltrimethylammonium chloride for the didecyldimethylammonium chloride to yield dodecyltrimethylammonium borate.

EXAMPLE 142
Didecyldimethylammonium 2-ethylhexanoate

The procedure of Example 134 was followed, substituting 2-ethylhexanoic acid for the propionic acid.

A cloudy product resulted.

EXAMPLE 143
Didecyldimethylammonium octanoate

The procedure of Example 134 was followed, substituting octanoic acid for the propionic acid.

EXAMPLE 144
Didecyldimethylammonium polyacrylate

The procedure of Example 134 was followed, substituting polyacrylic acid for the propionic acid.

Treatment of Wood Substrate

EXAMPLE 145
Didecyldimethylammonium acetate

End grain pine wafers were weighed and then soaked with didecyldimethylammonium acetate in ethanol/water until a weight gain of 45% was observed.

The treated wafers were then placed in water and weighed periodically to determine resistance to leaching.

Figure 1B:
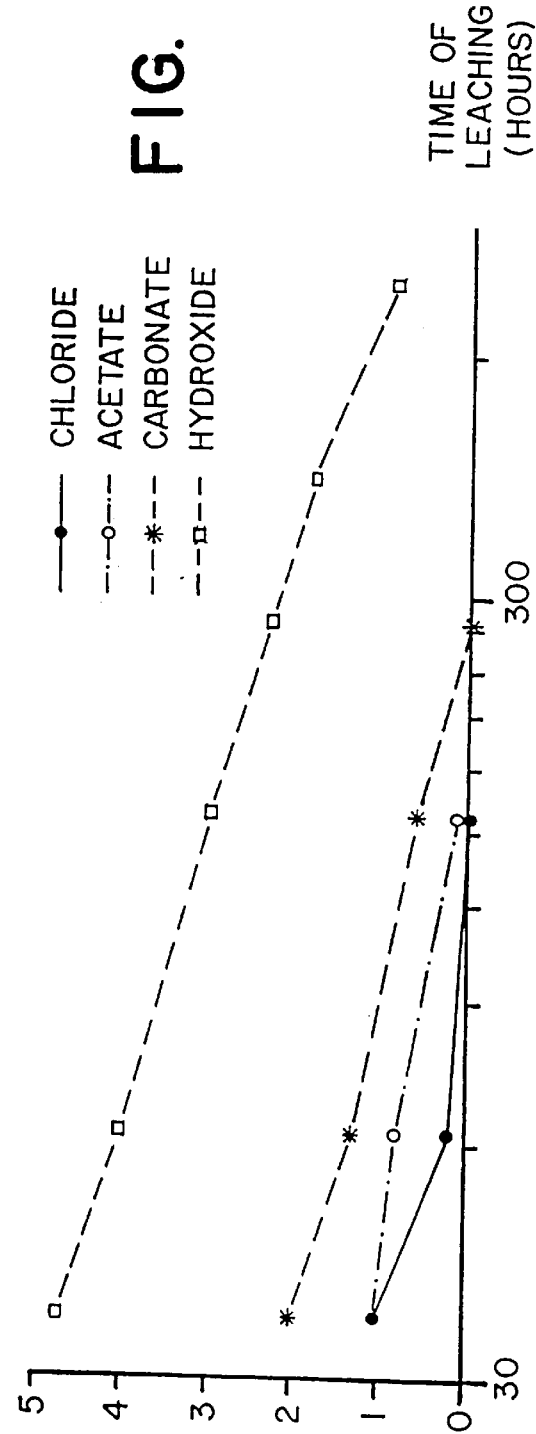
FIG. 1B is an enlarged segment of the graph of FIG. 1A.

Results are illustrated in FIGS. 1A, 1B, and 1C.

Comparative Example 145A
Didecyldimethylammonium chloride

End grain pine wafers were weighed and then soaked with didecyldimethylammonium chloride in 20% ethanol/water until a weight gain of 35% was observed.

The treated wafers were then placed in water and weighed periodically to determine resistance to leaching.
Results are illustrated in FIGS. 1A, 1B and 1C.

EXAMPLE 146
Didecyldimethylammonium borate
End grain pine wafers were weighed and then soaked with didecyldimethylammonium borate in ethanol/water until a weight gain of 30% was observed.
The treated wafers were then placed in water and weighed periodically to determine resistance to leaching.
Results are illustrated in FIGS. 1A and 1B.

EXAMPLE 147
Didecyldimethylammonium methacrylate
End grain pine wafers were weighed and then soaked with didecyldimethylammonium methacrylate in ethanol/water until a weight gain of 30% was observed.
The treated wafers were then placed in water and weighed periodically to determine resistance to leaching.
Results are illustrated in FIGS. 1A and 1B.

EXAMPLE 148
Didecyldimethylammonium gluconate
End grain pine wafers were weighed and then soaked with didecyldimethylammonium gluconate in ethanol/water until a weight gain of 30% was observed.
The treated wafers were then placed in water and weighed periodically to determine resistance to leaching.
Results are illustrated in FIGS. 1A and 1B.

EXAMPLE 149
Didecyldimethylammonium propionate
End grain pine wafers were weighed and then soaked with didecyldimethylammonium propionate in ethanol/water until a weight gain of 30% was observed.
The treated wafers were then placed in water and weighed periodically to determine resistance to leaching.
Results are illustrated in FIGS. 1A and 1B.

EXAMPLE 150
Didecyldimethylammonium 2-ethylhexanoate
End grain pine wafers were weighed and then soaked with didecyldimethylammonium ethylhexanoate in ethanol/water until a weight gain of 35% was observed.
The treated wafers were then placed in water and weighed periodically to determine resistance to leaching.
Results are illustrated in FIG. 1C.

EXAMPLE 151
Didecyldimethylammonium laurate
End grain pine wafers were weighed and then soaked with didecyldimethylammonium laurate in ethanol/water until a weight gain of 35% was observed.
The treated wafers were then placed in water and weighed periodically to determine resistance to leaching.
Results are illustrated in FIG. 1C.

EXAMPLE 152
Didecyldimethylammonium decanoate
End grain pine wafers were weighed and then soaked with didecyldimethylammonium decanoate in ethanol/water until a weight gain of 30% was observed.
The treated wafers were then placed in water and weighed periodically to determine resistance to leaching.
Results are illustrated in FIG. 1C.

EXAMPLE 153
Didecyldimethylammonium stearate
End grain pine wafers were weighed and then soaked with didecyldimethylammonium stearate in ethanol/water until a weight gain of 40% was observed.
The treated wafers were then placed in water and weighed periodically to determine resistance to leaching.
Results are illustrated in FIG. 1C.

EXAMPLE 154
Didecyldimethylammonium stearate emulsion
End grain pine wafers were weighed and then soaked with didecyldimethylammonium stearate emulsion in water until a weight gain of 6% was observed.
The treated wafers were then placed in water and weighed periodically to determine resistance to leaching.
Results are illustrated in FIG. 1C.

EXAMPLE 155
Didecyldimethylammonium octanoate
End grain pine wafers were weighed and then soaked with didecyldimethylammonium octanoate in water until a weight gain of 40% was observed.
The treated wafers were then placed in water and weighed periodically to determine resistance to leaching.
Results are illustrated in FIG. 1C.
FIGS. 1A, 1B, and 1C illustrate that the carboxylate quats of the present invention resist leaching for extended periods of time, and better than the chloride quat.

EXAMPLE 156
Didecyldimethylammonium acetate/water
A 10"×0.5"×0.75" piece of ponderosa pine was equilibrated, weighed, and heated for two hours at 60° C. The wood was treated with a treating solution of 2% didecyldimethylammonium acetate in water by heating in the solution at 60° C. to 80° C. for one hour, cooling and standing overnight, and then being subjected to a second warm to cool cycle. The samples were allowed to dry to constant weight, and the uptake was determined by comparing starting and finishing weights.
The samples were then heated for two hours at 60° C., and the weight of the warm treated samples was compared to the oven dried sticks before treatment.
Results are illustrated in Table 1.

Comparative Example 156A
Water
The procedure of Example 156 was followed, omitting the didecyldimethylammonium acetate from the treating solution.
Results are illustrated in Table 1.

Comparative Example 156B
Didecyldimethylammonium chloride/water
The procedure of Example 156 was followed, substituting a treating solution of 2% didecyldimethylammonium chloride in water for the treating solution.
Results are illustrated in Table 1.

EXAMPLE 157
Didecyldimethylammonium 2-ethylhexanoate/water
The procedure of Example 156 was followed, substituting a treating solution of 2t didecyldimethylammonium 2-ethylhexanoate in water for the treating solution.
Results are illustrated in Table-1.

EXAMPLE 158
Didecyldimethylammonium mixed coconut fatty acid carboxylate/water The procedure of Example 156 was followed substituting a treating solution of 2% didecyldimethylammonium mixed coconut fatty acid in water for the treating solution.

Results are illustrated in Table 1.

EXAMPLE 159
Didecyldimethylammonium acetate/ammonia water

The procedure of Example 156 was followed substituting a treating solution of 1% didecyldimethylammonium acetate in 3% ammonia water for the treating solution.

Results are illustrated in Table 1.

Comparative Example 159A
Ammonia water

The procedure of Comparative Example 156A was followed, omitting the didecyldimethylammonium acetate from the treating solution.

Results are illustrated in Table 1.

Comparative Example 159B
Didecyldimethylammonium chloride/-ammonia water

The procedure of Comparative Example 156B was followed substituting a treating solution of 1% didecyldimethylammonium chloride in 3% ammonia water for the treating solution.

Results are illustrated in Table 1.

EXAMPLE 160
Didecyldimethylammonium 2-ethylhexanoate/ammonia water

The procedure of Example 156 was followed substituting a treating solution of it didecyldimethylammonium 2-ethylhexanoate in 3% ammonia water for the treating solution.

Results are illustrated in Table 1.

EXAMPLE 161
Didecyldimethylammonium mixed coconut fatty acid carboxylate/ammonia water The procedure of Example 156 was followed substituting a treating solution of 1% didecyldimethylammonium mixed coconut fatty acid in 3% ammonia water for the treating solution.

Results are illustrated in Table 1.

EXAMPLE 162
Didecyldimethylammonium acetate/aqueous acetic acid

The procedure of Example 156 was followed substituting a treating solution of 2% didecyldimethylammonium acetate in 10% aqueous acetic acid for the treating solution.

Results are illustrated in Table 1.

Comparative Example 162A
Aqueous acetic acid

The procedure of Example 156A was followed omitting the didecyldimethylammonium acetate.

Results are illustrated in Table 1.

Comparative Example 162B
Didecyldimethylammonium chloride/-aqueous acetic acid The procedure of Example 156B was followed substituting a treating solution of 2% didecyldimethylammonium chloride in 10% aqueous acetic acid for the treating solution.

Results are illustrated in Table 1.

EXAMPLE 163
Didecyldimethylammonium 2-ethylhexanoate/aqueous acetic acid

The procedure of Example 156 was followed substituting a treating solution of 2% didecyldimethylammonium 2-ethylhexanoate in 10% aqueous acetic acid for the treating solution.

Results are illustrated in Table 1.

EXAMPLE 164
Didecyldimethylammonium mixed coconut fatty acid carboxylate/aqueous acetic acid The procedure of Example 156 was followed substituting a treating solution of 2% didecyldimethylammonium mixed coconut fatty acid carboxylate in 10% aqueous acetic acid for the treating solution.

Results are illustrated in Table 1.

TABLE 1

| Weight Uptake From Quat Solutions | | | | | | | | |
| --- | --- | --- | --- | --- | --- | --- | --- | --- |
| Example | 156 | 156A | 156B | 157 | 158 | 159 | 159A | 159B |
| Solvent | Water | Water | Water | Water | Water | 3% Ammonia | 3% Ammonia | 3% Ammonia |
| Quat | Acetate | — | Chloride | 2-Ethyl-Hexanoate | Mixed Coconut Fatty Acid Carboxylate | Acetate | — | Chloride |
| Weight Uptake (%) | 0.9 | −0.4 | 0.6 | 3.6 | 3.7 | 2.8 | −0.6 | 2 |
| Example | 160 | 161 | 162 | 162A | 162B | 163 | 164 | |
| Solvent | 3% Ammonia | 3% Ammonia | 10% Acetic Acid | 10% Acetic Acid | 10% Acetic Acid | 10% Acetic Acid | 10% Acetic Acid | |
| Quat | 2-Ethyl Hexanoate | Mixed coconut fatty acid carboxylate | Acetate | — | Chloride | 2-Ethyl-Hexanoate | Mixed Coconut Fatty Acid Carboxylate | |
| Weight Uptake (%) | 6.0 | −0.3 | 1.8 | 0.7 | 1.1 | 4.9 | 2.3 | |

Examples 156–164 when compared with Comparative Examples 156A, 156B, 159A, 159B, 162A and 162B, illustrate the ability of carboxylate quats of the present invention to be applied to wood substrates. The carboxylate quats are absorbed better than chloride quats in water and aqueous acetic acid, while most carboxylate quats are comparable in ammonia water. However, the carboxylate quats can be used without metal coupling agents in treating wood substrates.

EXAMPLE 165
Didecyldimethylammonium acetate/water

A piece of wood was treated according to the procedure of Example 156. The piece of wood was then soaked in water at room temperature for 24 hours, dried to a constant weight, and weighed to determine how much chemical remained. The piece of wood was soaked for 96 additional hours (120 hours total), dried to constant weight, and weighed to determine the leaching of the quat from the treated wood. The water was changed several times during this period.

Results are illustrated in Table 2.

Comparative Example 165A

Water

A piece of wood was treated according to the procedure of Comparative Example 156A. The piece of wood was then soaked according to the procedure of Example 165.

Results are illustrated in Table 2.

Comparative Example 165B

Didecyldimethylammonium chloride/water

A piece of wood was treated according to the procedure of Comparative Example 156B. The piece of wood was then soaked according to the procedure of Example 165.

Results are illustrated in Table 2.

EXAMPLE 166

Didecyldimethylammonium 2-ethylhexanoate/water

A piece of wood was treated according to the procedure of Example 157. The piece of wood was then soaked according to the procedure of Example 165.

Results are illustrated in Table 2.

EXAMPLE 167

Didecyldimethylammonium mixed coconut fatty acid carboxylate/water

A piece of wood was treated according to the procedure of Example 158. The piece of wood was then soaked according of the procedure of Example 165.

Results are illustrated in Table 2.

EXAMPLE 168

Didecyldimethylammonium acetate/ammonia water

A piece of wood was treated according to the procedure of Example 159. The piece of wood was then soaked according to the procedure of Example 165.

Results are illustrated in Table 2.

Comparative Example 168A

Ammonia water

A piece of wood was treated according to the procedure of Comparative Example 159A. The piece of wood was then soaked according to the procedure of Example 165.

Results are illustrated in Table 2.

Comparative Example 168B

Didecyldimethylammonium chloride/ammonia water

A piece of wood was treated according to the procedure of Comparative Example 159B. The piece of wood was then soaked according to the procedure of Example 165.

Results are illustrated in Table 2.

EXAMPLE 169

Didecyldimethylammonium 2-ethylhexanoate/ammonia water

A piece of wood was treated according to the procedure of Example 160. The piece of wood was then soaked according to the procedure of Example 165.

Results are illustrated in Table 2.

EXAMPLE 170

Didecyldimethylammonium acetate/aqueous acetic acid

A piece of wood was treated according to the procedure of Example 162. The piece of wood was then soaked according to the procedure of Example 165.

Results are illustrated in Table 2.

Comparative Example 170A

Aqueous acetic acid

A piece of wood was treated according to the procedure of Comparative Example 162A. The piece of wood was then soaked according to the procedure of Example 165.

Results are illustrated in Table 2.

Comparative Example 170B

Didecyldimethylammonium chloride/aqueous acetic acid

A piece of wood was treated according to the procedure of Comparative Example 162B. The piece of wood was then soaked according to the procedure of Example 165.

Results are illustrated in Table 2.

EXAMPLE 171

Didecyldimethylammonium 2-ethylhexanoate aqueous acetic acid

A piece of wood was treated according to the procedure of Example 163. The piece of wood was then soaked according to the procedure of Example 165.

Results are illustrated in Table 2.

EXAMPLE 172

Didecyldimethylammonium mixed coconut fatty acid carboxylate/aqueous acetic acid A piece of wood was treated according to the procedure of Example 164. The piece of wood was then soaked according to the procedure of Example 165.

Results are illustrated in Table 2.

TABLE 2

| | Leaching of Quat | | | | | | |
|---|---|---|---|---|---|---|---|
| Example | 165 | 165A | 165B | 166 | 167 | 168 | 168A |
| Solvent | Water | Water | Water | Water | Water | 3% Ammonia | 3% Ammonia |
| Quat | 2% Acetate | — | 2% Chloride | 2% 2-Ethyl-Hexanoate | 2% Mixed Coconut Fatty Acid Carboxylate | 2% Acetate | |
| Weight Uptake (%) | 0.9 | −0.4 | 0.6 | 3.6 | 3.7 | 2.8 | −0.6 |
| Retained Quat at 24 Hours (Absolute %/Relative %) | 1.2/133 | −0.2/— | 0.5/83 | 2.5/67 | 3.5/97 | 1.5/54 | −0.3/— |
| Retained Quat at 120 Hours | 1/110 | −0.2/— | 0.4/67 | 2/55 | 2.9/97 | 1/36 | −0.3/— |

TABLE 2-continued

Leaching of Quat (Absolute %/Relative %)

| Example | 168B | 169 | 170 | 170A | 170B | 171 | 172 |
|---|---|---|---|---|---|---|---|
| Solvent | 3% Ammonia | 3% Ammonia | 10% Acetic Acid | 10% Acetic Acid | 10% Acetic Acid | 10% Acetic Acid | 10% Acetic Acid |
| Quat | 2% Chloride | 2% 2-Ethyl-Hexanoate | 2% Acetate | — | 2% Chloride | 2% 2-Ethyl-Hexanoate | 2% Mixed Coconut Fatty Acid Carboxylate |
| Weight Uptake (%) | 2.0 | 6.0 | 1.8 | 0.7 | 1.1 | 4.9 | 2.3 |
| Retained Quat at 24 Hours (Absolute %/Relative %) | 1.7/85 | 3.8/63 | 0.9/50 | −1.0/— | −0.1/0 | 2.8/57 | — |
| Retained Quat at 120 Hours (Absolute %/Relative %) | 1.3/65 | 4.5/75 | 0.4/8 | −1.3/— | −1/— | 1.9/39 | — |
| Swell Index (%) | — | — | — | — | — | — | — |

Examples 165–172 and Comparative Examples 165A, 165B, 168A, 168B, 170A, and 170B demonstrate the relative retention properties of carboxylate quats and chloride quats. In most instances the carboxylate quats are more leach resistant than chloride quats. However, carboxylate quats will not require metal couplers for long term leaching resistance.

Biocidal Activity

EXAMPLE 173

Didecyldimethylammonium acetate

Cultures of *A. niger, G. trabeum, T. veride*, and *L. lepideus* were inoculated with varying amounts of 75% of didecyldimethylammonium acetate in water. The concentrations of carboxylate quat at which no growth was observed and the highest concentration at which growth was not affected were averaged.

Results are illustrated in Table 3.

Comparative Example 173A

Didecyldimethylammonium chloride

The procedure of Example 173 was followed, substituting didecyldimethylammonium chloride for the didecyldimethylammonium acetate.

Results are illustrated in Table 3.

Comparative Example 173B

Didecyldimethylammonium chloride/iodopropargyl butylcarbamate

The procedure of Example 173 was followed, substituting a mixture of 4 parts of didecyldimethylammonium chloride and 1 part of iodopropargyl butylcarbamate for the didecyldimethylammonium acetate.

Results are illustrated in Table 3.

EXAMPLE 174

Didecyldimethylammonium 2-ethylhexanoate

The procedure of Example 173 was followed, substituting didecyldimethylammonium 2-ethylhexanoate for the didecyldimethyl-ammonium acetate.

Results are illustrated in Table 3.

EXAMPLE 175

Didecyldimethylammonium laurate

The procedure of Example 173 was followed, substituting didecyldimethylammonium laurate for the didecyldimethylammonium acetate.

Results are illustrated in Table 3.

EXAMPLE 176

Didecyldimethylammonium stearate

The procedure of Example 173 was followed, substituting didecyldimethylammonium stearate for the didecyldimethylammonium acetate.

Results are illustrated in Table 3.

TABLE 3

Biocidal Minimum Effective Concentrations

| Example | 173 | 173A | 173B | 174 | 175 | 176 |
|---|---|---|---|---|---|---|
| Quat | Acetate | Chloride | Chloride Combo | 2-Ethyl-hexanoate | Laurate | Stearate |
| *A. niger* | >200 | 150 | 60 | 90 | 50 | 65 |
| *G. trabeum* | 7 | 5 | 1 | 5 | 5 | 5 |
| *T. veride* | 5 | 5 | 5 | 125 | 5 | 5 |
| *L. lepideus* | 10 | 5 | 1 | 100 | 75 | 5 |

Examples 173–176 illustrate that carboxylate quats are effective against a variety of microorganisms.

EXAMPLES 177–180

Didecyldimethylammonium acetate 1 ppm, 100 ppm, 200 ppm, and 400 ppm of didecyldimethyl-ammonium acetate in water were added to separate petri dishes containing agar. The tests were conducted by placing 5 mm agar discs with actively growing fungus face down onto the center of a prepared petri dish. The dish was then sealed with a strip of parafilm and incubated. The diameters of the cultures were measured every day after the growth of controls having no didecyldimethylammonium acetate added reached 3 cm in diameter, and measurement continued until the controls reached the side of the petri dish. If a culture grew in an irregular shape, two or more measurements were made and averaged. The amount of growth was compared to a control grown without any carboxylate quat added as described in Example 173.

Results are illustrated in Table 4.

Comparative Examples 177A-180A

Didecyldimethylammonium chloride

The procedures of Examples 177–180 were followed, substituting didecyldimethylammonium chloride for the didecyldimethylammonium acetate.

Results are illustrated in Table 4.

Comparative Examples 177B-180B

Didecyldimethylammonium chloride/iodopropargyl butylcarbamate

The procedures of Examples 177–180 were followed, substituting a mixture of 4 parts of didecyldimethylammonium chloride and 1 part of iodopropargyl butylcarbamate for the didecyldimethylammonium acetate.

Results are illustrated in Table 4.

EXAMPLES 181–184
Didecyldimethylammonium propionate

The procedures of Examples 177–180 were followed, substituting didecyldimethylammonium propionate for the didecyldimethylammonium acetate.

Results are illustrated in Table 4.

EXAMPLES 185–188
Didecyldimethylammonium laurate

Results are illustrated in Table 4.

EXAMPLES 197 and 198

Didecyldimethylammonium linolenate

The procedures of Examples 193 and 194 were followed, substituting didecyldimethyl linolenate for the didecyldimethylammonium stearate.

Results are illustrated in Table 4.

TABLE 4

| | | | | Biocidal Effect on T. Versicolor | | | | | | |
|---|---|---|---|---|---|---|---|---|---|---|
| Example | 177 | 177A | 177B | 178 | 178A | 178B | 179 | 179A | 179B | 180 |
| Anion | Acetate | Chloride | Chloride Combo | Acetate | Chloride | Chloride Combo | Acetate | Chloride | Chloride Combo | Acetate |
| Concentration (ppm) | 1 | 1 | 1 | 100 | 100 | 100 | 200 | 200 | 100 | 400 |
| Growth Reduction (%) | 6 | 19 | 19 | 69 | 73 | 78 | 74 | 77 | 91 | 79 |
| Example | 180A | 180B | 181 | 182 | 183 | 184 | 185 | 186 | 187 | 188 |
| Anion | Chloride | Chloride Combo | Propionate | Propionate | Propionate | Propionate | Laurate | Laurate | Laurate | Laurate |
| Concentration (ppm) | 400 | 400 | 1 | 100 | 200 | 400 | 1 | 100 | 200 | 400 |
| Growth Reduction (%) | 84 | 91 | 5 | 61 | 69 | 68 | 0 | 50 | 57 | 70 |
| Example | 189 | 190 | 191 | 192 | 193 | 194 | 195 | 196 | 197 | 198 |
| Anion | D-Gluconate | D-Gluconate | D-Gluconate | D-Gluconate | Stearate | Stearate | Linoleate | Linoleate | Linolenate | Linolenate |
| Concentration (ppm) | 1 | 100 | 200 | 400 | 50 | 250 | 50 | 250 | 50 | 250 |
| Growth Reduction (%) | 3 | 62 | 65 | 76 | 51 | 65 | 45 | 56 | 45 | 65 |

The procedures of Examples 177–180 were followed, substituting didecyldimethylammonium laureate for the didecyldimethylammonium acetate.

Results are illustrated in Table 4.

EXAMPLES 189–192
Didecyldimethylammonium D-gluconate

The procedures of Examples 177–180 were followed, substituting didecyldimethylammonium D-gluconate for the didecyldimethylammonium acetate.

Results are illustrated in Table 4.

EXAMPLES 193 and 194
Didecyldimethylammonium stearate 50 ppm and 250 ppm of didecyldimethylammonium stearate in water were added to separate petri dishes containing agar. 5 mm agar discs with actively growing culture of T. versicolor were placed in the center of each dish, and the amounts of each growth were compared to a control grown without any carboxylate quat added as described in Example 174.

Results are illustrated in Table 4.

EXAMPLES 195 and 196
Didecyldimethylammonium linoleate

The procedures of Examples 193 and 194 were followed, substituting didecyldimethylammonium linoleate for the didecyldimethylammonium stearate.

Examples 177–198 illustrate the biocidal effects of carboxylate quats.

EXAMPLES 199–202

Didecyldimethylammonium acetate

The procedures of Examples 177–180 were followed, substituting G. trabeum for T. versicolor.

Results are illustrated in Table 5.

Comparative Examples 199A-202A

Didecyldimethylammonium chloride

The procedures of Comparative Examples 177A-180A were followed, substituting G. trabeum for T. versicolor.

Results are illustrated in Table 5.

Comparative Examples 199B-202B

Didecyldimethylammonium chloride/idopropargyl butylcarbamate

The procedures of Comparative Examples 177B-180B were followed, substituting G. trabeum for T. versicolor.

Results are illustrated in Table 5.

EXAMPLES 203–206
Didecyldimethylammonium propionate

The procedures of Examples 181–184 were followed, substituting G. trabeum for T. versicolor.

Results are illustrated in Table 5.

EXAMPLES 207–210
Didecyldimethylammonium laurate

The procedures of Examples 185–188 were followed, substituting G. trabeum for T. versicolor.

Results are illustrated in Table 5.

EXAMPLES 211–214
Didecyldimethylanmonium d-gluconate

The procedures of Examples 189–192 were followed, substituting G. trabeum for T. versicolor.

Results are illustrated in Table 5.

EXAMPLES 215 and 216
Didecyldimethylammonium stearate

The procedure of Examples 193 and 194 were followed, substituting G. trabeum for T. versicolor.

Results are illustrated in Table 5.

EXAMPLES 217 and 218
Didecyldimethylammonium linoleate

The procedure of Examples 195 and 196 were followed, substituting G. trabeum for T. versicolor.

Results are illustrated in Table 5.

EXAMPLES 219 and 220
Didecyldimethylammonium linoleneate

The procedure of Examples 197 and 198 were followed, substituting G. trabeum for T. versicolor.

Results are illustrated in Table 5.

Examples 199–220 illustrate the biocidal effects of carboxylate quats.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

I claim:

1. A wood preservative system comprising
   (a) a wood preserving biocidal effective amount of a combination of
      (i) at least one di-$C_8$–$C_{12}$ alkyl quaternary ammonium carboxylate having the formula

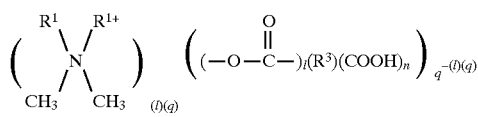

wherein $R^1$ is a $C_8$–$C_{12}$ alkyl group; $R^3$ is a substituted or unsubstituted, interrupted or uninterrupted $C_1$–$C_{100}$ group; l and q independently are 1, 2, or 3 and (l)(q) is 1, 2, or 3; and n is 0 or an integer from 1 to 50; and
      (ii) at least one quaternary ammonium borate having the formula

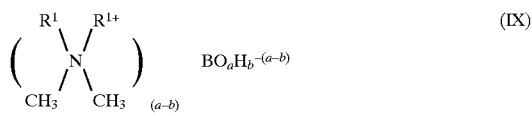

wherein $R^1$ is a $C_8$–$C_{12}$ alkyl group, a is 2 or 3, but when a is 2, b is 0 or 1, and when a is 3, b is 0, 1, or 2; and

TABLE 5

Biocidal Effect on G. trabeum

| Example | 199 | 199A | 199B | 200 | 200A | 200B | 201 | 201A | 201B | 202 |
|---|---|---|---|---|---|---|---|---|---|---|
| Anion | Acetate | Chloride | Chloride Combo | Acetate | Chloride | Chloride Combo | Acetate | Chloride | Chloride Combo | Acetate |
| Concentration (ppm) | 1 | 1 | 1 | 100 | 100 | 100 | 200 | 200 | 100 | 400 |
| Growth Reduction (%) | 29 | 36 | 42 | 69 | 89 | 89 | 72 | 89 | 89 | 89 |

| Example | 202A | 202B | 203 | 204 | 205 | 206 | 207 | 208 | 209 | 210 |
|---|---|---|---|---|---|---|---|---|---|---|
| Anion | Chloride | Chloride Combo | Propionate | Propionate | Propionate | Propionate | Laurate | Laurate | Laurate | Laurate |
| Concentration (ppm) | 400 | 400 | 1 | 100 | 200 | 400 | 1 | 100 | 200 | 400 |
| Growth Reduction (%) | 89 | 89 | 34 | 65 | 89 | 89 | 35 | 71 | 89 | 89 |

| Example | 211 | 212 | 213 | 214 | 215 | 216 | 217 | 218 | 219 | 220 |
|---|---|---|---|---|---|---|---|---|---|---|
| Anion | D-Gluconate | D-Gluconate | D-Gluconate | D-Gluconate | Stearate | Stearate | Linoleate | Linoleate | Linolenate | Linolenate |
| Concentration (ppm) | 1 | 100 | 200 | 400 | 50 | 250 | 50 | 250 | 50 | 250 |
| Growth Reduction (%) | 25 | 79 | 89 | 89 | 75 | 86 | 69 | 84 | 75 | 79 |

(b) an aqueous solvent; said wood preserving system being metal-free.

2. A wood preservative system as defined in claim 1 comprising from about 0.1 to about 5 parts by weight of a combination of di-$C_8$–$C_{12}$ alkyl quaternary ammonium carboxylate and di-$C_8$–$C_{12}$ alkyl quaternary ammonium borate and from about 95 to about 99.9 parts by weight of an aqueous solvent based upon 100 parts by weight of a combination of di-$C_8$–$C_{12}$ alkyl quaternary ammonium carboxylate and di-$C_8$–$C_{12}$ alkyl quaternary ammonium borate and aqueous solvent combined.

3. A wood preservative system as defined in claim 2 comprising from about 1 to about 2 parts by weight of a combination of di-$C_8$–$C_{12}$ alkyl quaternary ammonium carboxylate and di-$C_8$–$C_{12}$ alkyl quaternary ammonium borate and from about 98 to about 99 parts by weight of an aqueous solvent based upon 100 parts by weight of a combination of di-$C_8$–$C_{12}$ alkyl quaternary ammonium carboxylate and di-$C_8$–$C_{12}$ alkyl quaternary ammonium borate and aqueous solvent combined.

* * * * *